(12) United States Patent
Maerkl et al.

(10) Patent No.: US 8,039,269 B2
(45) Date of Patent: Oct. 18, 2011

(54) MECHANICALLY INDUCED TRAPPING OF MOLECULAR INTERACTIONS

(75) Inventors: Sebastian J. Maerkl, Palo Alto, CA (US); Stephen R. Quake, Stanford, CA (US)

(73) Assignee: California Institute of Technology, Pasadena, CA (US)

( * ) Notice: Subject to any disclaimer, the term of this patent is extended or adjusted under 35 U.S.C. 154(b) by 1056 days.

(21) Appl. No.: 11/698,757

(22) Filed: Jan. 26, 2007

(65) Prior Publication Data

US 2007/0224617 A1 Sep. 27, 2007

Related U.S. Application Data

(60) Provisional application No. 60/880,156, filed on Jan. 11, 2007, provisional application No. 60/880,209, filed on Jan. 11, 2007, provisional application No. 60/762,330, filed on Jan. 26, 2006, provisional application No. 60/762,344, filed on Jan. 26, 2006.

(51) Int. Cl.
*G01N 33/543* (2006.01)
(52) U.S. Cl. ..................................... 436/518
(58) Field of Classification Search .................. None
See application file for complete search history.

(56) References Cited

U.S. PATENT DOCUMENTS

| | | | | |
|---|---|---|---|---|
| 5,556,961 A * | 9/1996 | Foote et al. | ........... | 536/27.1 |
| 5,959,098 A * | 9/1999 | Goldberg et al. | ........... | 536/25.3 |
| 6,572,742 B1 * | 6/2003 | Cohen | ........... | 204/297.05 |
| 6,899,137 B2 * | 5/2005 | Unger et al. | ........... | 137/833 |
| 6,960,437 B2 * | 11/2005 | Enzelberger et al. | ........... | 435/6 |
| 7,143,785 B2 * | 12/2006 | Maerkl et al. | ........... | 137/597 |
| 2004/0007470 A1 * | 1/2004 | Smalley | ........... | 205/118 |
| 2004/0072278 A1 * | 4/2004 | Chou et al. | ........... | 435/29 |
| 2007/0248971 A1 | 10/2007 | Maerkl et al. | | |
| 2010/0154890 A1 * | 6/2010 | Maerkl et al. | ........... | 137/1 |

FOREIGN PATENT DOCUMENTS

WO  WO 2007/089587 A2  8/2007

OTHER PUBLICATIONS

PCT International Preliminary Examination Report of Jul. 29, 2008 for application PCT/US07/002176.
PCT Search Report mailed Apr. 24, 2008 for application PCT/US07/002176.
PCT Written Opinion mailed Apr. 24, 2008 for application PCT/US07/002176.
Van Dam, "Solvent-Resistant Elastomeric Mircofludic Devices and Applications, PhD Thesis", California Institute of Technology, 2005.

* cited by examiner

*Primary Examiner* — Ann Lam
(74) *Attorney, Agent, or Firm* — Kilpatrick Townsend & Stockton LLP

(57) ABSTRACT

The invention provides devices and methods for surface patterning the substrate of a microfluidic device, and for detection and analysis of interactions between molecules by mechanically trapping a molecular complex while substantially expelling solvent and unbound solute molecules. Examples of molecular complexes include protein-protein complexes and protein-nucleic acid complexes.

10 Claims, 13 Drawing Sheets
(10 of 13 Drawing Sheet(s) Filed in Color)

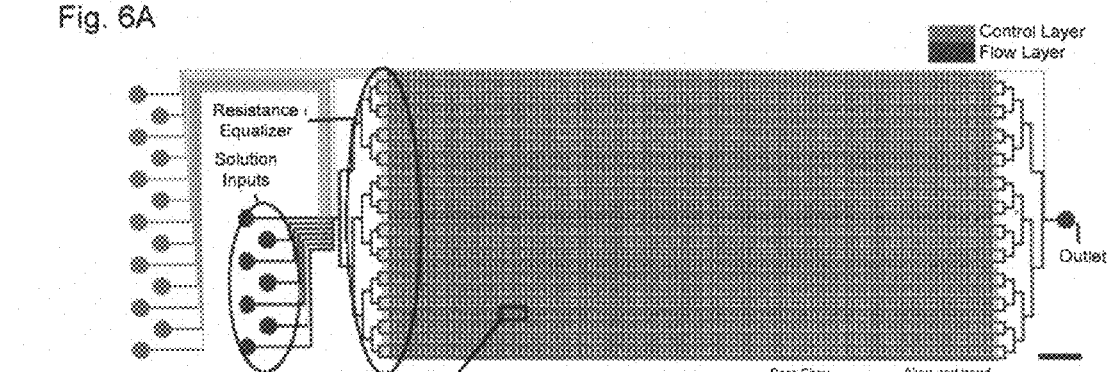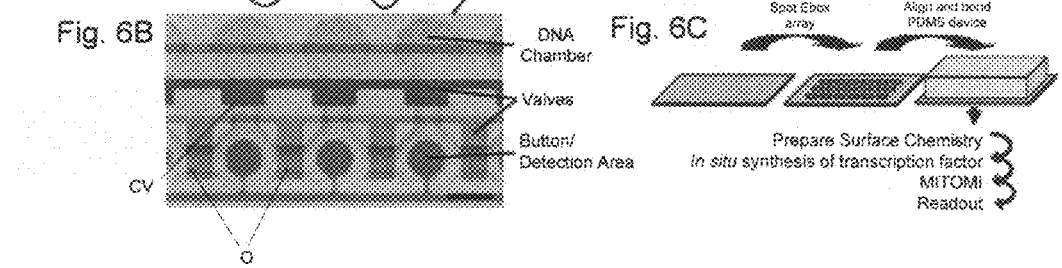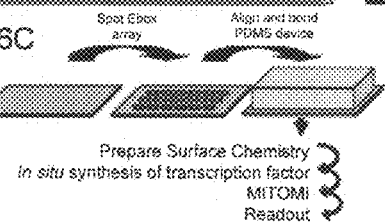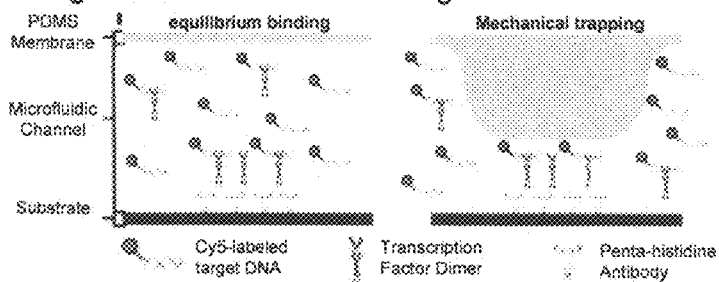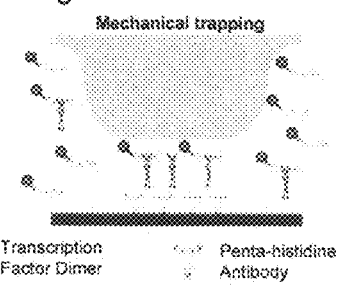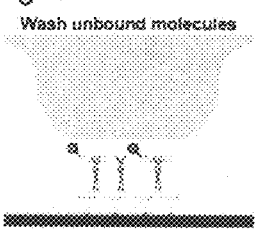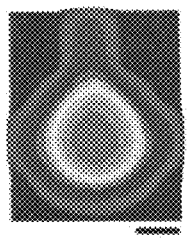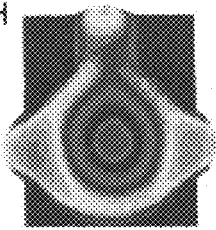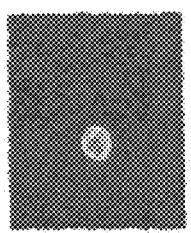

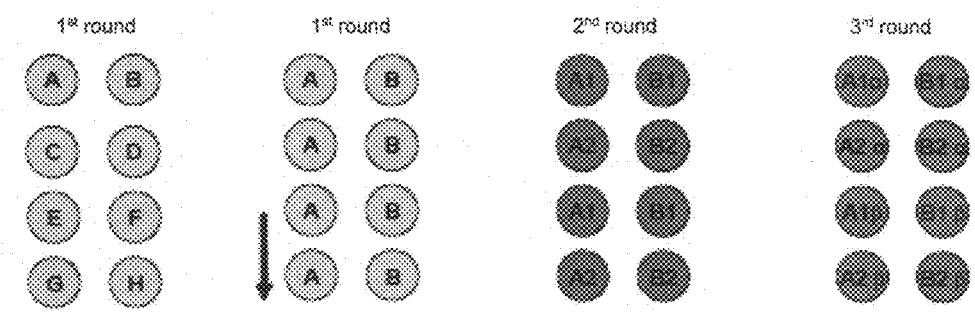
Fig. 7A.: Std. Array    Fig. 7B.: Co-multispotting
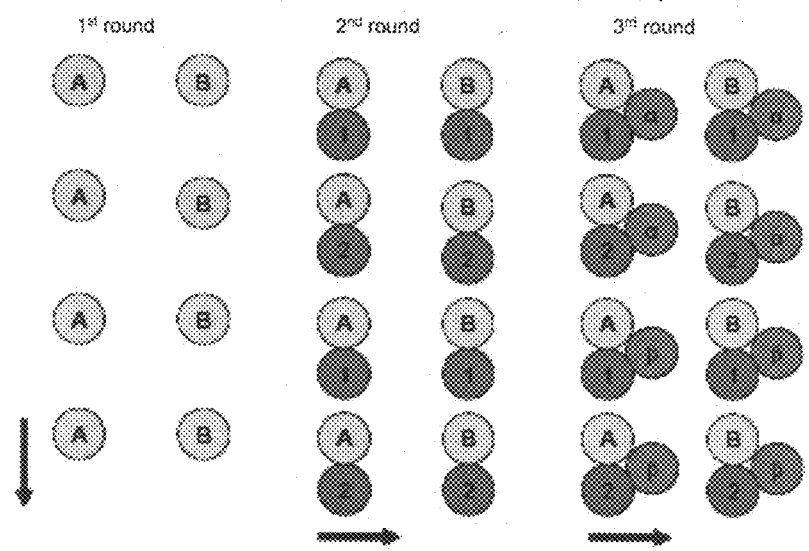
Fig. 7C.: Neighbor-multispotting

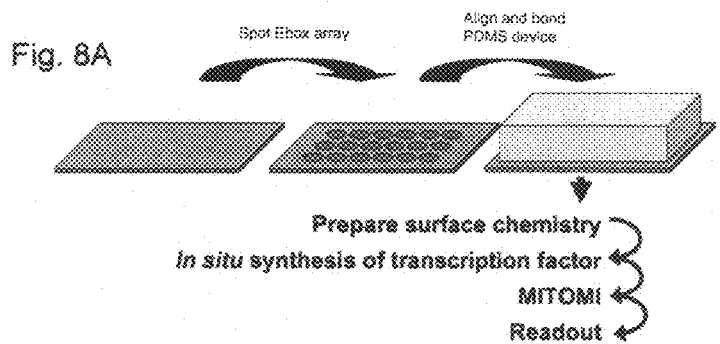
Fig. 8A
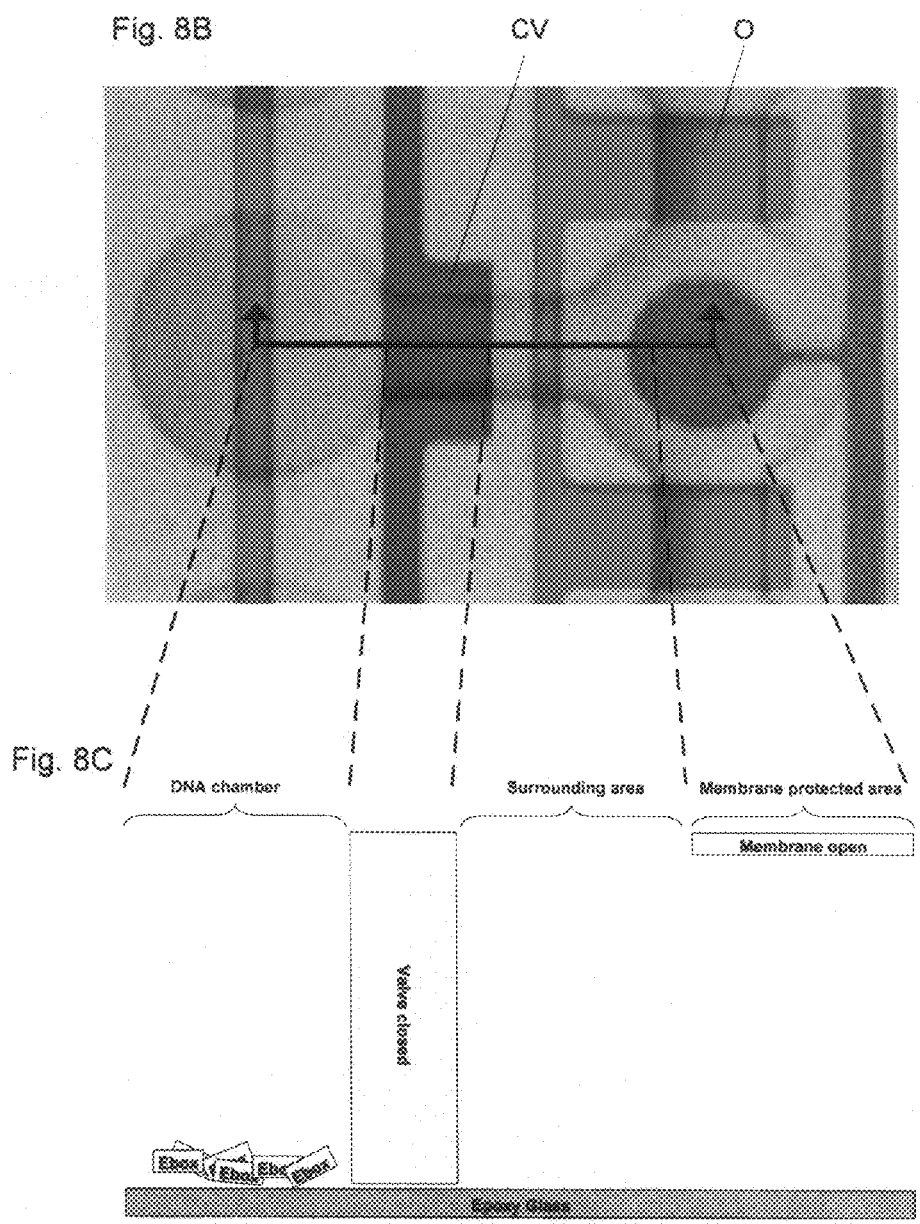
Fig. 8B
Fig. 8C

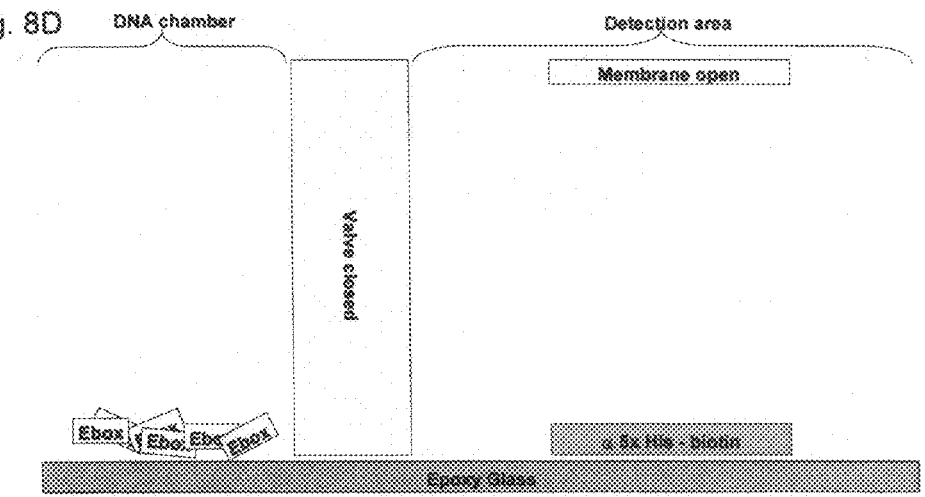
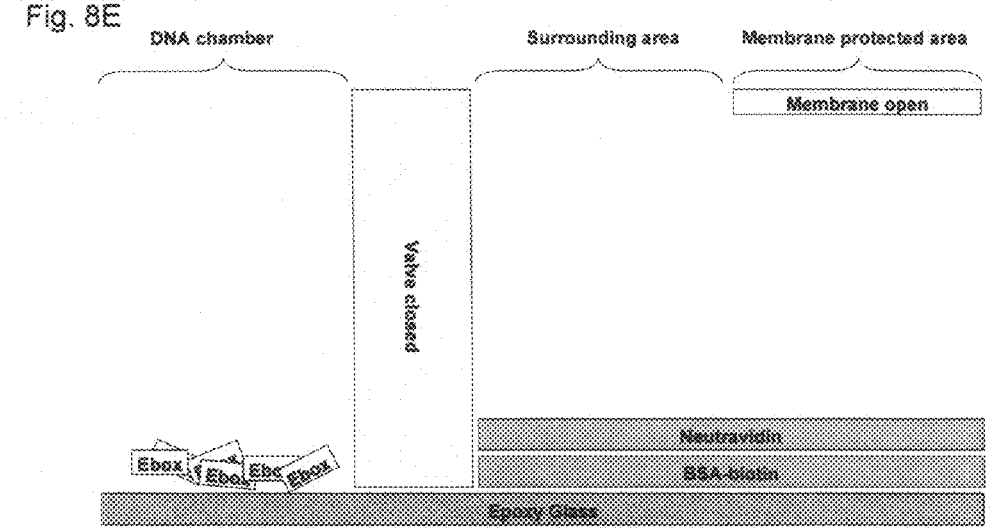
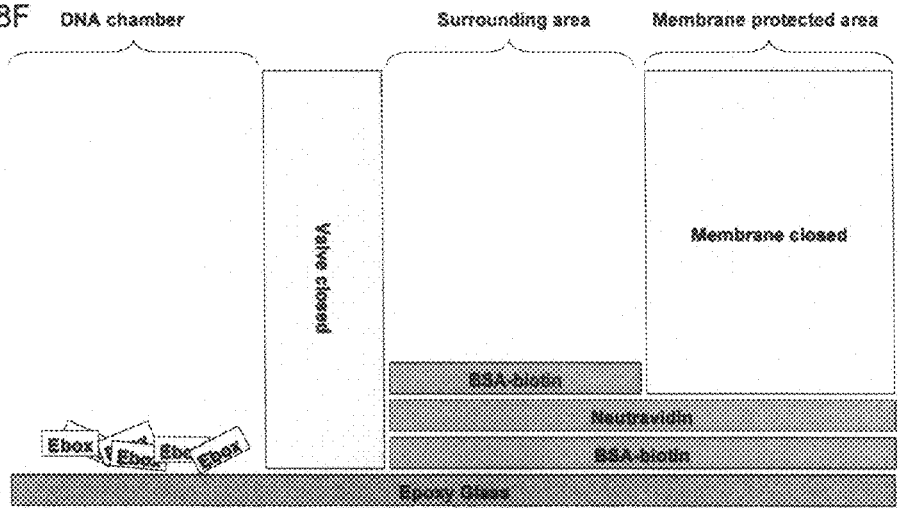

US 8,039,269 B2

MECHANICALLY INDUCED TRAPPING OF MOLECULAR INTERACTIONS

CROSS-REFERENCE TO RELATED APPLICATIONS

This application claims benefit of U.S. Provisional Application No. 60/762,330 entitled "Mechanically Induced Trapping of Molecular Interactions" and Provisional Application No. 60/762,344 entitled "Programming Microfluidic Devices with Molecular Information," both filed Jan. 26, 2006, and to U.S. Provisional Application No. 60/880,156 entitled "Mechanically Induced Trapping of Molecular Interactions" and U.S. Provisional Application No. 60/880,209 entitled "Programming Microfluidic Devices with Molecular Information", both filed Jan. 11, 2007. The entire content of each of these applications is incorporated herein by reference.

STATEMENT REGARDING FEDERALLY SPONSORED RESEARCH

Work described herein has been supported, in part, by the Office of Naval Research (ONR)—Space and Naval Warfare Systems Center (Grant No. N66001-02-1-8929; Subcontract Princeton 341-6260-515). The United States Government may have certain rights in the invention.

FIELD OF THE INVENTION

The invention relates to novel microfluidic devices and use of microfluidic devices for analysis of interactions between molecules (e.g., biomolecules and/or chemical compounds). The invention finds application in the fields of biology, chemistry, medicine and microfluidics.

BACKGROUND

Analysis of molecular interactions involving biomolecules, such as proteins, nucleic acids, and glycans, is central to understanding biological processes and is a critical step in drug development. However, quantifying the affinity of molecular interactions is a considerable technical challenge. First, there are often a large number of variables that govern any particular biological interaction. Therefore obtaining equilibrium dissociation constants, for example, requires one to perform dozens of assays as the concentrations of various components are systematically varied, increasing the number of measurements needed in an already logistically challenging process. A second and more fundamental problem is the fact that many molecular interactions are transient in nature and exhibit nanomolar to micromolar affinities, leading to rapid loss of bound material or little bound material in the first place. These factors are problematic for high-throughput methods such as yeast two-hybrid and tandem affinity purification mass spectrometry where transient interactions are frequently missed. Protein-protein and protein-DNA binding microarrays (PBMs) are especially susceptible due to their stringent wash requirements, causing rapid loss of weakly bound material. Protein arrays have been applied to quantify ligand-ErbB receptor interactions with off-rates determined by surface plasmon resonance to be on the order of $10^{-4}$ $s^{-1}$. PBMs have been applied in a semiquantitative manner to transcription factor (TF) motif analysis for high affinity interactions, with off-rates on the order of $10^{-3}$ $s^{-1}$.

BRIEF SUMMARY OF THE INVENTION

In one aspect, the invention provides a method for selectively modifying the substrate in a unit cell of a microfluidic device by (i) masking a first portion of the substrate by contacting the first portion with a moveable element of the unit cell; (ii) contacting non-masked regions of the substrate with a substrate modifying agent; (iii) depleting or removing the substrate modifying agent; and (iv) unmasking the first portion of the substrate. In one embodiment the movable element is a deflectable elastomeric membrane. In one embodiment the deflectable elastomeric membrane is free-standing. In one embodiment contact between the membrane and the substrate occurs medially and extends radially outward.

In one version of the method the substrate modifying agent covalently modifies the substrate. In one version the substrate modifying agent noncovalently modifies the substrate. In one version the substrate modifying agent is a protein or a nucleic acid. In one version the substrate modifying agent is an antibody, a receptor, a fusion protein, a glycan, a lipid, or a carbohydrate. In one version the substrate modifying agent is conjugated to avidin or biotin. In one version the substrate has previously been selectively modified.

In one aspect the invention provides a method using a unit cell of a microfluidic device, said unit cell comprising in a liquid environment: a substrate, a molecular complex comprising a first molecule immobilized in a contact area of the substrate, and second molecule bound to the first molecule and thus indirectly bound to the substrate, and a trapping element that upon actuation contacts the substrate in the contact area of the substrate. The method includes actuating the trapping element causing it to contact the substrate in the contact area thereby physically trapping the first and second molecules bound to the substrate in the contact area while substantially expelling solvent and solute molecules. In one embodiment, the method includes detecting the trapped first and/or second molecules.

In one embodiment, the method includes the step of de-actuating the trapping element and, optionally, detecting the first and/or second molecules after deactuation.

In one embodiment, prior to de-actuating the trapping element, the liquid environment in the unit cell is changed. In one embodiment, prior to actuating the trapping element the complex is contacted with a third molecule and the effect of the third molecule on formation or dissociation of the complex is determined. In various illustrative versions of the invention, the first molecule is an antibody and the second molecule is an antigen or the first molecule is a protein and the second molecule is molecule bound by the protein.

In one aspect the invention provides a method using a unit cell of a microfluidic device, said unit cell comprising in a liquid environment a substrate, a first molecule immobilized in a contact area of the substrate, a second molecule, a movable element that upon actuation contacts the substrate in the contact area of the substrate, where the method includes actuating the movable element causing it to contact the substrate in the contact area thereby physically trapping the first molecule and any second molecules bound to the first molecule substantially expelling solvent and unbound second molecules. In one embodiment, the method includes the step of de-actuating the movable element. In one embodiment, the method is carried out on at least 100 unit cells of a microfluidic device, and each of the 100 unit cells comprises a different first molecule and/or a different second molecule and/or optionally a different third molecule.

In one aspect, the invention provides a method of fabricating a microfluidic device by i) positioning an elastomeric block comprising a plurality of chamber recesses and a solid support comprising a microarray of discrete reagent-containing regions so as to align each reagent-containing region with a recess; ii) adhering the block to the solid support so as to produce a plurality of chambers containing reagents wherein each reagent-containing region contains two or more discrete subregions, each containing a different reagent. In one aspect, the solid support is epoxy-functionalized glass. In one various illustrative embodiments i) the microarray has a density of 100 or more discrete regions per cm$^2$ or has a density of 1000 or more discrete regions per cm$^2$; ii) the microarray comprises 10 or more different reagents or 100 or more different reagents or 500 or more different reagents. In some embodiments the reagents are proteins, nucleic acids, or small organic molecules.

In one aspect, the invention provides a microfluidic device comprising a plurality of unit cells, each unit cell comprising a microfluidic flow channel having a substrate, a microfluidic chamber overlying the flow channel, wherein said channel and said chamber are separated by elastomeric membrane and wherein an increase in pressure in the chamber causes the membrane to deflect into the channel and contact the substrate of the flow channel; and a second chamber in fluidic communication with the flow channel comprising a reagent in dry form disposed on a reagent-containing region of the substrate wherein at least 100 unit cells of the device each contains a different reagent, different amounts of a reagent, or a different combination of reagents.

In one aspect, the invention provides a microfluidic device comprising a plurality of unit cells, each unit cell comprising: a flow channel having a substrate, a membrane actuator chamber overlying the flow channel and separated from the flow channel by an elastomeric membrane and, where an increase in pressure in the chamber causes the membrane to deflect into the channel and contact the substrate of the channel; and a third chamber in fluidic communication with the flow channel; each first chamber is in fluidic communication with a first chamber in two adjacent unit cell(s), a valve that can be closed to fluidically separate the first and third chambers, a valve or valves that can be closed to fluidically separate the first chamber from first chambers in adjacent unit cells.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2A shows the final surface chemistry just prior to introduction of the in vitro transcription/translation reagents. Each grey block represents a monolayer consisting of the indicated molecule. FIG. 2B provides the process of protein synthesis using the deposited linear expression templates. The synthesized MAX iso A protein diffuses to the antibody coated surface and is pulled down via its N-terminal 6× Histidine tag. The free Ebox DNA molecules, introduced with the ITT mix, are recognized by MAX iso A and likewise pulled down to the surface. In FIG. 2C MITOMI is performed by closure of the button membrane, trapping any bound material and expunging any unbound material (corresponding image: FIG. 2D shows the final state of the device after the last PBS wash removing any unbound material from the adjacent material (corresponding image.

FIGS. 3A-3C shows testing the dependence of the actual spot size on membrane diameter. FIG. 3A shows an Autocad diagram of a section of the actual device. Here 5 unit cells with different membrane diameters are shown. Heavy lines indicate control lines and light lines indicate flow lines. Membrane diameters are 180 μm on the far left decreasing to 100 μm in 20 μm steps. The actual device has one additional unit cell with a 80 μm membrane. FIG. 3B shows the fluorescence [seen as dark areas] of Cy5 labeled DNA templates filled in the flow channel. The membranes have been closed trapping DNA bound by a surface bound transcription factor. Note the halo of low intensity around the spots, indicative of low non-specific binding of templates due to the membrane action. FIG. 3C shows the same area of the device as FIG. 3B after flushing the flow channel with PBS with the membranes remaining closed to prevent loss of bound material.

FIG. 6A shows a design drawing of the microfluidic device. Red [dark] and blue [light] lines represent control and flow channels, respectively. The device contains 2,400 unit cells controlled by 7,233 valves (scale bar=2 mm). FIG. 6B shows an optical micrograph of three unit cells. Control channels are filled with colored food dyes for visualization. Each unit cell consists of a DNA chamber aligned to a microarray spot, and a detection area. The valves colored green (marked "cv") control access to the DNA chambers while the valves colored orange ("o") compartmentalize the unit cells. The button membrane represents the area where detection takes place (scale bar=150 μm). FIG. 6C shows a schematic outline of the approach. First a microarray of target DNA sequences is spotted onto an epoxy slide. The microarray is then aligned and bonded to a microfluidic device. Next the necessary surface chemistry is prepared, followed by in situ synthesis of TF and detection of interactions by MITOMI. FIGS. 6D-6F provide a schematic of the process of MITOMI. The gray structure at the top of each panel represents the deflectable button membrane that may be brought into contact with the glass surface ("substrate"). FIG. 6D shows that His5 tagged TFs are localized to the surface and TF-DNA binding is in a steady state. FIG. 6E shows that the button membrane is brought into contact with the surface, expelling any solution phase molecules while trapping surface bound material. FIG. 6F shows that unbound material not physically protected is washed away and the remaining molecules are quantified. FIGS. 6G-6I are fluorescent intensity maps of target DNA concentration, corresponding to the states schematically shown in FIGS. 6D-6F (scale bar=50 μm).

FIG. 7 illustrates three approaches to printing micro-arrays for use with microfluidic devices. Circles indicate array spots and the label (A, B, 1, 2, alpha, beta) identifies the contents of the spot. Arrows indicate the preferred direction in which spots are deposited (only certain arrows are shown). FIG. 7A depicts a standard micro-array where each spot is unique and originates from a unique solution. FIG. 7B shows a co-multispotted pattern in which over three rounds a three dimensional matrix is generated. First columns are spotted with the solutions A and B respectively, followed by spotting of solutions 1 and 2 in the respective rows directly on top of the previously spotted solutions. In the third round solutions alpha and beta are spotted. FIG. 7C illustrates "neighbor multispotting." The array in FIG. 7C is similar to that in FIG. 7B, except that spots are placed adjacent to, rather than on top of, one another.

DETAILED DESCRIPTION

Definitions

Figure 1A:
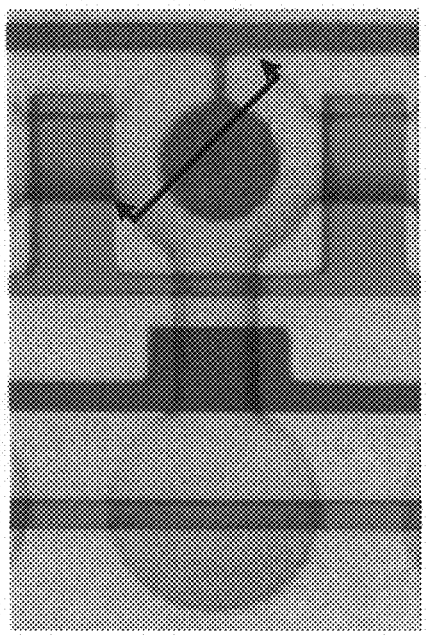
FIGS. 1A-1D show a close-up view of a unit cell with control lines filled with colored food dyes and empty flow layer. The blue control line [b] creates the button membrane [bm] shown in the open (FIGS. 1A and 1C) and closed (FIGS. 1B and 1D) configurations. Panels C and D show a schematic of a cross-section through the correlating image along the arrow-demarcated black lines.
Figure 1B:
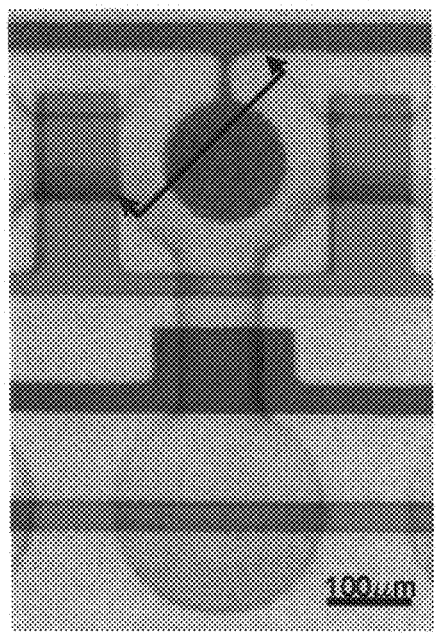
Figure 1C:
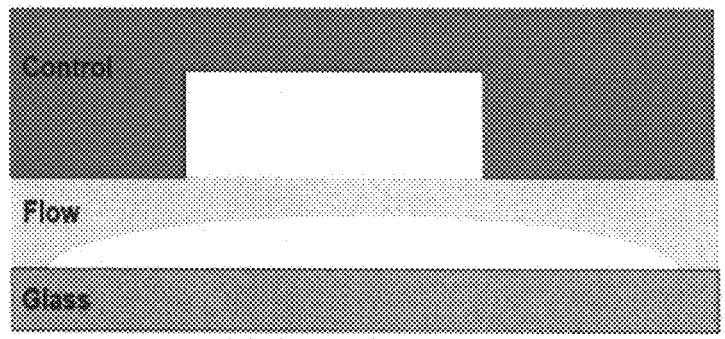
Figure 1D:
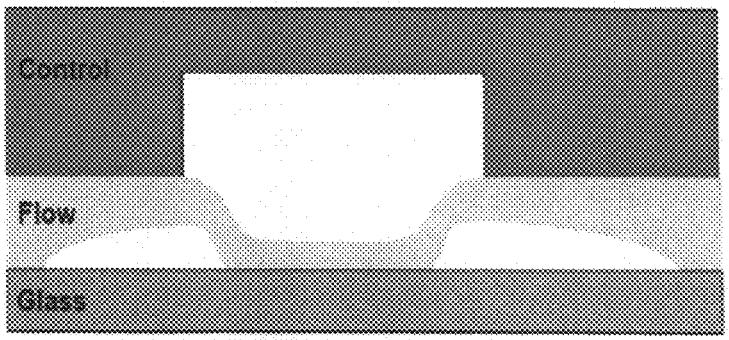

As used herein, the term "microfluidic" device has its normal meaning in the art and refers to a device with structures (channels, channels, chambers, valves and the like) at least some of which have at least one dimension on the order of tens or hundreds of microns. In general, at least one structure of the device has dimension(s) below 1000 microns.

As used herein, "elastomeric" has its normal meaning in the microfluidic arts. Elastomers in general are polymers existing at a temperature between their glass transition temperature and liquefaction temperature. See Allcock et al., Contemporary Polymer Chemistry, 2nd Ed. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials may be characterized by a Young's modulus. Elastomeric materials having a Young's modulus of between about 1 Pa-1 TPa, more preferably between about 10 Pa-100 GPa, more preferably between about 20 Pa-1 GPa, more preferably between about 50 Pa-10 MPa, and more preferably between about 100 Pa-1 MPa are useful in accordance with the present invention, although elastomeric materials having a Young's modulus outside of these ranges could also be utilized depending upon the needs of a particular application. Given the tremendous diversity of polymer chemistries, precursors, synthetic methods, reaction conditions, and potential additives, there are a huge number of possible elastomer systems that could be used to make the devices of the invention. Common elastomeric polymers include perfluoropolyethers, polyisoprene, polybutadiene, polychloroprene, polyisobutylene, poly(styrene-butadiene-styrene), polyurethanes, and silicones, for example, or poly(bis(fluoroalkoxy)phosphazene) (PNF, Eypel-F), poly(carborane-siloxanes) (Dexsil), poly(acrylonitrile-butadiene) (nitrile rubber), poly(I-butene), poly(chlorotrifluoroethylene-vinylidene fluoride) copolymers (KeI-F), poly(ethyl vinyl ether), poly(vinylidene fluoride), poly(vinylidene fluoride-hexafluoropropylene) copolymer (Viton), elastomeric compositions of polyvinyl chloride (PVC), polysulfone, polycarbonate, polymethylmethacrylate (PMMA), and polytertrafluoroethylene (Teflon), polydimethylsiloxane, polydimethylsiloxane copolymer, and aliphatic urethane diacrylate.

As used herein, "unit cell" refers to a combination of microfluidic structural elements that is repeated many times (e.g., 48 to 10,000 times, 100 to 5,000 times, or 250-2500 times) in a microfluidic device, where unit cells can operate simultaneously to carry out a function in a highly parallel manner.

As used herein, "substrate" refers to a surface in a chamber or channel in a microfluidic device. Usually a chamber or channel can be defined by reference to substantially planar surfaces (e.g., floor, ceiling, and walls) and "substrate" refers to a particular planar surface, e.g., the "floor." More particularly, "substrate" refers to an exposed surface and may change over time. For example, in a microfluidic chamber in which one surface is formed by a solid support (e.g., an epoxy glass slide) coated with BSA, the substrate is the BSA layer. If this substrate is uniformly derivatized with an NHS-ester biotin to produce a biotin layer, the substrate is the biotin layer. If one portion of the biotin layer is derivatized by binding streptavidin, the substrate is the biotin layer in some regions (those not derivatized) and the streptavidin layer in other regions (derivatized regions). In a unit cell, a "chamber substrate" refers to the substrate in a chamber, a "channel substrate" refers to the substrate in a channel, and a "unit cell substrate" refers to a substrate in any region of the unit cell.

As used herein, a trapping element such as a trapping membrane or button membrane is "free-standing" if, when actuated (i) at least some portion of the membrane is in contact with the substrate of a flow channel and (ii) the membrane does not contact the side walls of the flow channel.

As used herein, the verb "mask" refers to the process of physically contacting and covering a portion of a unit cell substrate so as to exclude a substrate modifying agent and prevent the covered portion from being modified by the substrate modifying agent.

As used herein, the term "elastomeric block" refers to the elastomeric portion of a microfluidic device made using multilayer soft lithography techniques, which has not yet been adhered to a solid support (or substrate). The elastomeric block contains a plurality of "chamber recesses" that, upon attachment of the solid support form chambers in which the solid substrate forms one surface (e.g., the "floor").

As used herein, the term "flow channel" refers to a microfluidic channel through which a solution can flow. The dimensions of flow channels can vary widely but typically include at least one cross-sectional dimension {e.g., height, width, or diameter) less than 1 mm, preferably less than 0.5 mm, and often less than 0.3 mm. Flow channels often have at least one cross-sectional dimension in the range of 0.05 to 1000 microns, more preferably 0.2 to 500 microns, and more preferably 10 to 250 microns. The channel may have any suitable cross-sectional shape that allows for fluid transport, for example, a square channel, a circular channel, a rounded channel, a rectangular channel, etc. In an exemplary aspect, flow channels are rectangular and have widths of about in the range of 0.05 to 1000 microns, more preferably 0.2 to 500 microns, and more preferably 10 to 250 microns. In an exemplary aspect, flow channels have depths of 0.01 to 1000 microns, more preferably 0.05 to 500 microns, more preferably 0.2 to 250 microns, and more preferably 1 to 100 microns. In an exemplary aspect, flow channels have width-to-depth ratios of about 0.1:1 to 100:1, more preferably 1:1 to 50:1, more preferably 2:1 to 20:1, and most preferably 3:1 to 15:1, and often about 10:1. A flow channel need not have a uniform width along its length and, as described below, may be wider in the region in which the detection area is situated in order to accommodate a trapping membrane or other trapping element. For example the portion of the channel substrate that contains the detection region may be widened (i.e., wider than other portions of the flow channel) and/or rounded (see FIG. 1A and FIG. 3). Such a flow channel can be referred to as a "bulged flow channel." The portion of the channel substrate that contains the detection region can be widened and rounded, as noted, or have a different shape.

General Materials and Fabrication Methods

Materials and methods for producing a variety of microfluidic devices are known in the art. For illustration and not limitation, a brief discussion of useful methods is provided infra in the section entitled "General materials and fabrication methods."

Introduction

In one aspect the invention provides a microfluidic device having a plurality of unit cells, where each unit cell contains (i) a microfluidic flow channel and (ii) a moveable element that upon actuation can contact and mask a portion of the channel substrate.

In a second, related, aspect, the invention relates to methods for "surface patterning" a substrate of a microfluidic device by (i) masking a first portion of the substrate of a microfluidic channel; (ii) contacting non-masked regions of the channel with a substrate modifying agent; (iii) and unmasking the first portion. This results in a substrate that has both modified and unmodified regions and may be used to, for example, bind macromolecules to predetermined regions of a microfluidic substrate.

In a third, related, aspect, the invention relates to a method for detecting molecular interactions, referred to as "mechanically induced trapping of molecular interactions" or MITOMI. In MITOMI, a micro-mechanical membrane makes contact with a surface, physically trapping all surface bound molecules in the contact area, while expelling any unbound solvent and solute molecules. The trapped molecules may then be directly observed and/or tested against other compounds subsequently introduced into the system. The principal idea of this approach, the physical trapping of molecular interactions, is portable and thus applicable to a wide variety of systems and methods involving interactions between any kind of molecule. In some embodiments, a micro-mechanical membrane makes contact with a surface upon pressure dependent deflection (i.e., a pressure-actuated deflection).

In one example, MITOMI is used for fluid exchange in a microfluidic channel having an immobilized molecular complex in which one member of the complex is bound directly to the substrate and a second member of the complex is bound to the first member. Fluid exchange is accomplished without loss of bound material. Trapping of bound material protects it from subsequent wash and fluid exchange steps allowing background molecules to be removed and secondary reagents to be introduced into the system without disturbing the trapped material, allowing highly sensitive secondary assays such as ELISAs to be performed on this platform.

In one example, MITOMI is used to detect or characterize a molecular interaction for example (but not limited to) specific binding, binding affinity, association or disassociation rates and the effect of one molecule on an interaction between two other molecules.

Microfluidic Devices

MITOMI, surface patterning, and fluid exchange according to the present invention can be carried out using devices made using a wide variety of materials and with a variety of designs. In this section, for illustration and not for limitation, exemplary devices (which are particularly adapted for these processes) are described. For convenience, microfluidic devices of the invention can be referred to as "MITOMI devices," although, as will be apparent from the discussion below, the devices described herein may be used for surface patterning and other uses in addition to MITOMI.

In one aspect the invention provides a MITOMI microfluidic device having a plurality of unit cells, where each unit cell contains (i) a microfluidic flow channel and (ii) a moveable element (a "trapping element") that upon actuation can contact and mask a portion of the flow channel substrate.

The flow channel may have a variety of shapes and configurations. In one embodiment the contact area is in a bulged flow channel.

The portion of the channel substrate that is contacted by the trapping element is called the "contact area" or "mask area" or "detection area." These terms are used interchangeably and refer to the same area of the substrate in different contexts: the area contacted by the trapping element, which area is masked (preventing access by a substrate modifying agent) and where detection of trapped molecules occurs in MITOMI.

The trapping element may be a deflectable membrane or a non-membrane structure that can be actuated to contact a channel substrate (e.g., an elastomeric pad on a micromechanical extension arm). When the trapping element is in the form of a deflectable (e.g., elastomeric) membrane it may be free-standing or not free-standing. In one embodiment the trapping element is a free-standing deflectable membrane and is called a "trapping membrane". A generally circular trapping membrane can be called a "button membrane" or "button." In one embodiment the trapping membrane is elastomeric.

Movement of the trapping element is controlled by an actuator. Movement (i.e., deflection) of a deflectable membrane, such as a trapping membrane, can be controlled by a membrane actuator.

Microfluidic devices for use according to the invention may be fabricated using any of variety of methods, materials and configurations. In a particular embodiment the device is made using the techniques of multilayer soft lithography (MSL) and is referred to as an "MSL-type" device. To illustrate the invention, an MSL-type device with trapping membrane, is discussed in detail in subsection (a), infra. Alternative embodiments are then discussed in subsection (b), infra.

a) MSL-Type MITOMI Device

In one embodiment the MITOMI device is made using elastomeric materials using MSL fabrication techniques. Elastomeric devices made using MSL are well known, and familiarity with such devices by the reader is assumed in the description herein. (Additional guidance can be found in the scientific and patent literature, including references provided in the section "General Materials and Fabrication Methods" infra.) Briefly, MSL-type devices typically include (i) a flow layer, in which are situated flow channels through which liquids (including liquids containing analytes and reagents) can be transported; (ii) a solid support forming a surface (e.g., floor) of flow channels; and (iii) a control layer in which are situated control channels that overlay and intersect flow channels. At regions in which a control channel in the control layer overlies a flow channel in the flow layer, the lumens of the flow channel and control channel are separated by a thin membrane of elastomer. Increasing pressure in the control channel causes the thin membrane to be deflected into the flow channel, thereby acting as a valve that blocks flow of liquid through the channel. Reducing the pressure in the control channel allows the membrane to retract out of the flow channel, opening the valve and allowing fluid to pass through.

The MSL-type MITOMI device also contains a flow layer, a control layer and a solid support and has specialized features for adapted for MITOMI and surface patterning. In one embodiment the MSL-type MITOMI device has numerous (e.g., 48 to 10,000 or more) unit cells having the following basic components:

i) a microfluidic flow channel situated in the flow layer, one surface of the flow channel being the substrate surface;
ii) a membrane actuator chamber in the control layer adjacent to (e.g., overlying) the flow channel;
iii) an elastomeric trapping membrane separating the membrane actuator chamber and the microfluidic flow channel.

In this embodiment the membrane actuator chamber is connected to a control channel by a thin via so that the chamber can be hydraulically or pneumatically pressurized. Pressurization of the chamber causes its floor (which in effect is the membrane separating the chamber from the flow channel) to collapse and ultimately make contact with, or mask, the channel substrate. As alluded to above, this process can be used for masking to produce a substrate with both modified and unmodified regions, to trap, or protect, bound material for assays and analysis, and the like.

In certain respects, although they have very different functions, the trapping membrane in this embodiment is structurally similar to a monolithic valve because both are elastomeric membranes deflected into a flow channel. However, the trapping membrane in relation to the flow channel is structurally distinct from a valve in one or more (depending in the design of the device) of the following respects:

1. The trapping membrane is a free-standing membrane, i.e., when actuated it contacts the channel substrate without contacting the sides of the channel; and/or
2. The trapping membrane when fully actuated does not block flow of fluid through the flow channel; and/or
3. The trapping membrane when actuated contacts a circular area of the flow channel substrate; and/or
4. The trapping membrane contacts the flow channel substrate in a bulged region of the flow channel; and/or
5. The trapping membrane does not block passage of particles, such as a particle having a diameter of 5 to 50 microns, such as more than about 5 microns, such as more than 10 microns, such as more than 20 microns, such as more than 30 microns.

Particular trapping membranes can be characterized by any one or combination of the properties listed above.

FIG. 1 illustrates a unit cell of an illustrative MITOMI device. The actuator chamber is connected to a control channel on the same layer as the chamber itself by a thin via so that the button chamber can be hydraulically or pneumatically pressurized. FIGS. 1A to 1D illustrate the substrate ("glass"), flow layer containing a bulged flow channel, a control layer containing a membrane actuator chamber overlying the flow channel, and a trapping membrane separating the actuator chamber and flow channel. FIGS. 1A and 1B are micrographs showing the trapping membrane in an open (1A) and closed (1B) position. The round chamber shown in the bottom half of FIGS. 1A and 1B is a reagent chamber, which is discussed infra. In one design the actuator chamber is a smaller circular chamber aligned above the bulged flow channel. The circular chamber is connected to a channel on the same layer as the chamber itself by a thin via so that the chamber may be hydraulically or pneumatically pressurized. Pressurization of the chamber causes its floor, which in effect is the membrane separating the chamber from the bottom flow channel to collapse and ultimately make contact with the floor of the flow channel beneath (see FIG. 1 panels C and D) It is necessary that the valve geometry and closing pressure are adjusted so that the valve membrane contacts only a portion of the substrate (i.e., is not completely closed).

An increase in pressure in the membrane actuator chamber causes the trapping membrane to deflect into the flow channel and make contact with the channel substrate. In one embodiment, contact of the trapping membrane with the floor occurs centrically (e.g., starts closing at the middle of the membrane and then extends laterally outward as more of the membrane contacts the surface). As a consequence of this centric contact essentially no solvent molecules are trapped between the membrane and the floor of the flow channel (detection area). This drastically reduces the occurrence of non-specifically trapped solutes. In one embodiment a circular membrane closes radially (i.e., contact with the substrate begins at the approximate center of the membrane and radiates outward in a progressive manner).

In one design, the trapping membrane is generally circular (see FIG. 1) and can be referred to as a "button membrane" or "button." Although a circular trapping membrane which contacts the channel floor centrically works particularly well in the applications described herein, non-circular button membranes also can be used, as discussed below. The diameter of a button membrane is generally in the range 0.1 microns to 1,000 microns, often in the range 1 micron to 500 microns and usually in the range 10 microns to 500 microns.

Contact areas of various shapes (e.g., rectangular, circular, etc.) and sizes may be achieved by varying the geometry of the trapping membrane. geometries have been so far achieved (rectangular on the poster and circular in the disclosure). The size of the area of contact between the trapping membrane and substrate (the "contact area" or "mask area") can be precisely modulated by choice of button diameter and closing pressures (see FIG. 4 and Example 1). Typically the diameter of the contact area is generally in the range 0.1 microns to 1,000 microns, often in the range 1 micron to 500 microns and usually in the range 5 microns to 400 microns. It will be appreciated the size of the contact area is generally a fraction of the size of the flow channel in which it resides. In some embodiments the diameter of a circular contact area is not more than 75% of the width of the flow channel substrate at the location of the contact area, sometimes not more than 50% and sometimes not more than 25%. Usually the contact area extends less that the width of the flow channel. In some embodiments, the contact area extends not more than 75% of the width of the flow channel, sometimes not more than 50% and sometimes not more than 25% of the width of the flow channel. In contrast, the area of contact of a conventional monolithic valve with the substrate extends the entire width of the channel.

Closing pressures are generally in the range 12 and 18 psi, although other pressure ranges may be appropriate depending on configuration and material. Useful closing pressures range from 0.1 psi to 100 psi, usually in the range 1 psi to 50 psi, and more often in the range 10 to 20 psi.

In one embodiment of the invention having a generally circular trapping membrane, the membrane actuator chamber is also generally circular, or more precisely coin-shaped, with a diameter corresponding to that of the button membrane. It will be appreciated that the membrane actuator chamber of a pressure-actuated MSL-type device is connected by a via to control channels to actuate the membrane so that the membrane actuator chamber can be pressurized causing the membrane to deflect. In general the membrane actuator chamber and button membrane have diameters smaller than the underlying flow channel.

As noted, the shape and size of the flow channel near the contact area may vary. For example, the flow channel may have any shape, so long as it is large enough for the deflectable membrane to deflect into the chamber and contact the substrate, preferably without contacting the flow channel walls. For example the flow channel may be circular, octagonal, rectangular and the like near the contact area.

The MITOMI contact area can be (and usually is) in a flow channel (which may be fluidically isolated). For illustration and not limitation, the isolated MITOMI contact area and reagent chambers often have volumes of about 0.5-1 mL. Exemplary isolated contact areas and reagent chambers may have a generally circular footprint and have dimensions including a diameter of about 10 to about 1000 microns, e.g., from about 200-300 microns, e.g., about 250 microns, and heights of from about 1 to about 200 microns, e.g., about 5 to about 20 microns, e.b., about 10 microns. Contact areas and chambers having a non-circular shape may have similar volumes.

Valves in the flow channel(s) may be used to fluidically isolate the contact area. In one embodiment the flow channel has the configuration shown in FIG. 1. In this case three mechanical valves can be closed to isolate the contact area.

A microfluidic device having a chamber with an overlying elastomeric membrane that can be deflected into the chamber have been described for metering by volume exclusion. See US 2002/0029814 para. [0454] et seq. This device contains a first elastomer layer with a control chamber overlying a second elastomer layer with a dead-end reaction chamber. The control chamber overlies and is separated from dead-end reaction chamber by an elastomeric membrane. A reactant "x" may be introduced under pressure into dead-end reaction chamber. Increased control chamber pressure causes the elastomeric membrane to flex downward into reaction chamber, reducing by volume V the effective volume of reaction chamber. This in turn excludes an equivalent volume V of reactant from reaction chamber such that volume V of first reactant X is output from the flow channel. These metering structures differ in function and structure from the unit cells of a MITOMI device. For example, the MITOMI contact area can be (and usually is) in a flow channel (which may be fluidically isolated), while the metering structure is a dead-end reaction chamber. Further, when actuated the membrane of a metering structure does not contact the chamber substrate.

Although not discussed above, it will be understood that the unit cell can contain additional channels, valves, chambers, and other microfluidic elements, and the microfluidic device can include structures and functional units other than the unit cells described.

Alternative Device Embodiments

As noted, one concept of the invention is the physical trapping of molecular interactions, and is applicable to a wide variety of systems. Essentially in order to perform MITOMI two prerequisites are required: surface bound molecules to be detected and a second structure that makes contact with the surface and in doing so expels any non-bound substance from the surface. In principal any two structures which can be brought into contact and fulfill above requirements are sufficient for this approach and any surface chemistry that is specific and material compatible may be used. Similarly, surface patterning requires a substrate and a structure that masks the substrate and excludes a substrate modifying agent.

Figure 1E:
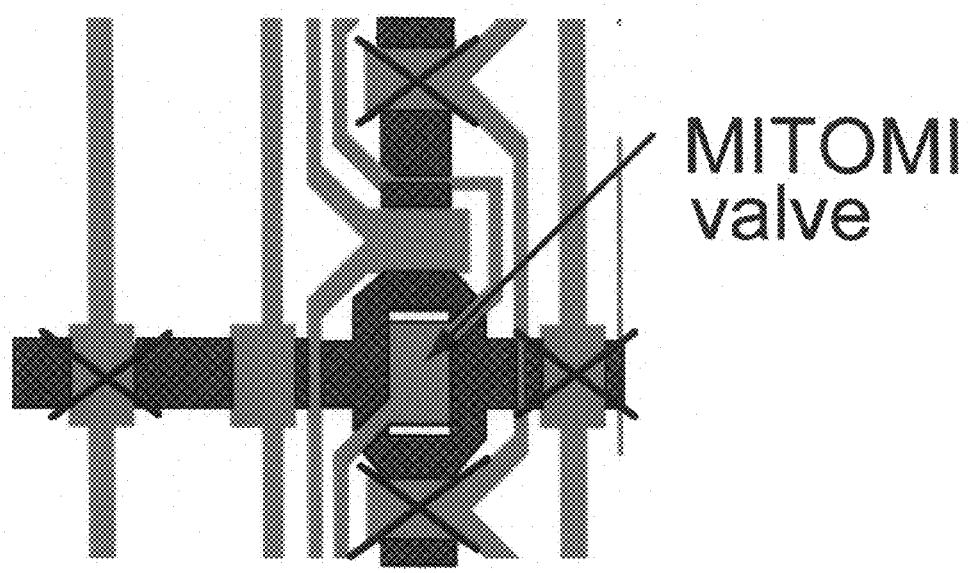
FIG. 1E shows one alternative design of a trapping element. Flow channels (red/gray) and control channels (cross hatched) are shown. White rectangles are "posts." Closing the valves marked with X defines the unit cell.
Figure 2A:
FIGS. 2A-2D show a schematic of the surface chemistry that was generated on the device as well as the process of protein synthesis, capture and MITOMI. Boxes indicate fluorescently labeled molecules. MAX iso A=fluorescein label; template=Cy3 label and Ebox=Cy5 label.
Figure 2B:
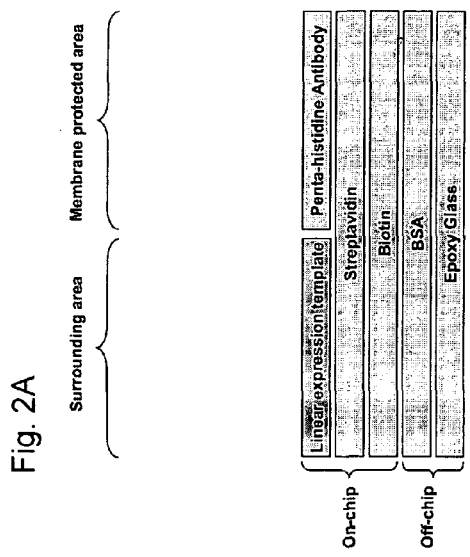
Figure 2D:
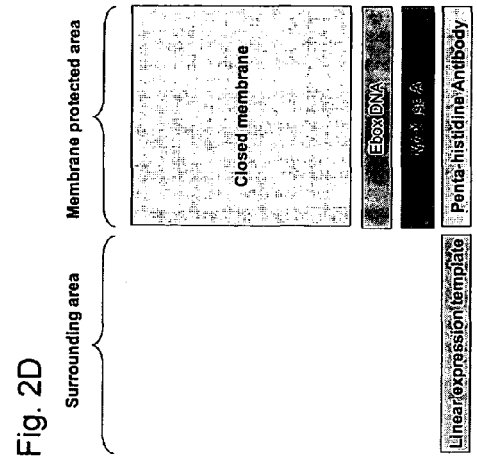
Figure 2C:
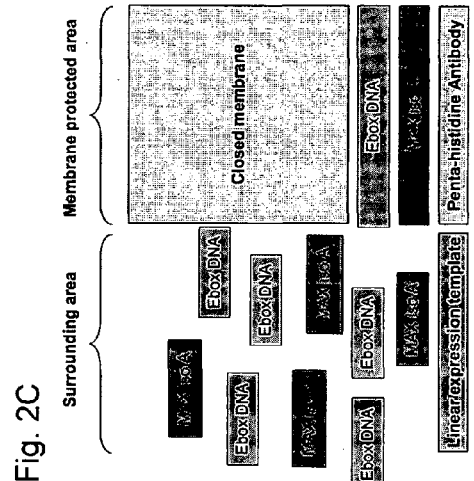

Variations on the MITOMI device described above include (i) devices with an elastomeric trapping membrane, but not produced using MSL; (ii) devices in which actuation of the membrane is not effected by a change in pressure in a membrane actuator chamber; (iii) devices in which the trapping membrane is not generally circular; (iv) devices in which the trapping element is not free-standing; and (v) devices in which the trapping element is not a membrane. FIG. 1E shows one alternative design in which the membrane is supported on either side by two "posts" situated in a bulged flow channel. In this design a MITOMI site is formed by the intersection of two flow channels. Within the bulged flow channel two elastomeric "posts" or elongated "columns" (shown as white rectangles in the figure) extend from the substrate to ceiling. In response to an increase in pressure in the control channel (gray) the elastomeric membrane ("MITOMI valve") is deflected into the flow channels between the posts and contacts the substrate. Note that, in contract to the circular button membrane, which closes radially, the valve starts closing in a line extending from the center of each post and then extends laterally outward as more of the membrane contacts the surface.

In some embodiments, a hybrid device comprising an elastomeric deflectable membrane with remaining portions of the channels and chambers of the device being a composite structure made from non-elastomeric materials. See, e.g., U.S. Pat. Pub. No. US 2002/0029814.

In some embodiments of the invention, a button membrane is actuated by a mechanism other than pressure. For example, use of electrostatic, electrolytic, electrokinetic, magnetic, thermal and chemical actuation systems are also contemplated, as described in patent publication US2002/0029814 (paragraphs [0256] et seq.) in relation to actuation of valves. In some embodiments, devices in which the deflectable membrane is made using a thermoresponsive polymer gel.

In some embodiments of the invention, the trapping membrane is not generally circular and/or the trapping element is not free-standing. For example, in some embodiments, a conventional monolithic valve (formed from a flow channel and control channel) can be used for substrate patterning and MITOMI. In one version, using MSL with PDMS, a thin PDMS membrane is generated between two channels formed in the PDMS and stacked and bonded on top of one another. In one version a valve that acentrically blocks a flow channel, restricting flow on one side (i.e., along one wall) of the channel but not completely shutting flow down and not allowing flow along both walls of the channel (i.e., a "half-valve") is used for MITOMI, surface patterning and fluid exchange. "Half valves" extend from one wall of the channel 10% to 80% of the way into the channel (without touching the opposite wall), and can be made using a "blind" control channel that extends only part of the way across an elastomeric membrane over a flow channel.

In some embodiments, devices with nonelastomeric button membranes are used. In some embodiments, a nano electromechanical system (NEMS) or micro electromechanical system (MEMS) is used in which a structure other than an elastomeric membrane is deflected into a microfluidic chamber to mask a portion of the substrate. Examples of such movable elements include silicon membranes or cantilevers, metal membranes and cantilevers. These membranes may be actuated by hydraulic, pneumatic or optical pressure as well as magnetically, electrostatically or mechanically.

Reagent Chamber

In certain embodiments, the MITOMI unit cells includes a reagent chamber (called a "DNA chamber" in FIG. 6B) that is in fluidic communication with the flow channel (i.e., the detection area of the flow channel. See FIG. 1A-B and FIG. 6B. The reagent chamber and the flow channel can be fluidically isolated from each other (e.g., by closing a valve in the channel that separates them). By opening the valve, reagents in the reagent chamber can be delivered to the flow channel and reagents in the flow channel can be delivered to the reagent chamber. In some embodiments a microfluidic pump is used to move fluids between the chambers. Importantly, in some embodiments micromechanical valves can be closed so that the portion of the flow channel in which the detection area is situated is isolated from other unit cells and is in communication with the reagent chamber; and micromechanical valves can be closed so that the portion of the flow channel in which the detection area is situated is isolated from the reagent chamber.

In one aspect, a device of the invention contains a plurality of unit cells, each unit cell including a flow channel having a substrate and a contact area, a membrane actuator chamber overlying the contact area of the flow channel substrate, with the flow channel and chamber are separated by elastomeric membrane so that an increase in pressure in the chamber causes the membrane to deflect into the flow channel and contact the substrate; and a second chamber (reagent chamber) in fluidic communication with the flow channel. In an embodiment each reagent chamber is in fluidic communication via a flow channel with a detection area in the unit cell, each detection area is in fluidic communication via a flow channel with detection areas in two adjacent unit cells, and the device includes valves that can be actuated to fluidically separate the detection area in each unit cell from detection areas in other unit cells.

Reagents (solutes and reagents in solution or suspension) can be delivered to the reagent chamber via flow channels. Additionally or alternatively reagents can be delivered to the reagent chamber by "array spotting" as described below.

In one aspect the invention provides a unit cell with (i) a flow channel with contact area and (ii) a reagent chamber. In one embodiment the microfluidic device has a plurality of unit cells, and each unit cell has (i) a flow channel having a substrate, (ii) a membrane actuator chamber overlying the flow channel, where the flow channel and actuator chamber are separated by elastomeric membrane, typically a free-standing membrane, and where an increase in pressure in the actuator chamber causes the membrane to deflect into the flow channel and contact the substrate at the contact area; and (iii) a reagent chamber in fluidic communication with the flow channel and comprising a reagent in dry form disposed on the reagent-chamber substrate. In one embodiment at least 100 unit cells of the device each contain a different reagent, different amounts of a reagent (e.g., a dilution series, or a different combination of reagents).

In one aspect the invention provides a microfluidic device having a plurality of unit cells, each unit cell having a flow channel having a substrate and detection area, an actuator chamber overlying the flow channel, where the flow channel and actuator channel are separated by elastomeric membrane and where an increase in pressure in the actuator chamber causes the membrane to deflect into the flow channel and contact the substrate of the first chamber; and a reagent chamber; where each reagent chamber is in fluidic communication with a single detection area; and each detection area is in fluidic communication with a detection area in two adjacent unit cell(s); a valve that can be closed to fluidically separate the detection areas and valves can be closed to fluidically separate the detection areas and reagent chambers.

Surface Patterning Using a MITOMI Device

In one aspect, the invention relates to methods for "surface patterning" a substrate of a microfluidic device by (i) masking a first portion of the substrate of a microfluidic chamber or channel; (ii) contacting non-masked regions of the chamber or channel with a substrate modifying agent; (iii) and unmasking the first portion. This results in a substrate that has both modified and unmodified regions and may be used to, for example, bind macromolecules to predetermined regions of the device substrate. In one example, a trapping element, such as a micro-mechanical membrane, makes contact with a surface and protects the contacted surface from derivatization steps, allowing one to generate a distinctly different surface chemistry in the area where the membrane closes from the area surrounding the membrane.

Actuating the button membrane masks the region of the substrate in contact with the button membrane so that a surface modifying agent introduced into the flow channel or chamber is excluded from the masked region. By using the button membrane for surface protection, complex surface chemistries can be generated in a spatially defined area. By varying the design of the membrane or other movable element, surface features having a variety of shapes and sizes may be created. Using designs shown in the examples, we have generated circular features with a diameter as low as 33 µm, or about ½ of spot sizes achievable by common quill pen based spotting (TeleChem International Inc.). Using this design circular features with a diameter on the order of about 5-10 µm should be readily obtainable.

Using the button membrane for substrate masking can be used to generate concentric rings of surface modification consisting of different molecules. This is achieved by a stepwise decrease of actuation pressure causing the membrane to gradually disengage from the substrate, exposing previously unmodified regions of the protected area. These unprotected areas may then be stepwise modified with substrate modifying molecules.

For example, Example 1 describes a chip with a substrate comprised of an epoxy glass support coated with BSA (see FIG. 2). The substrate is uniformly derivatized first with a biotinoyl-epsilon-aminocaproic acid-N-hydroxysuccinimide ester (NHS-ester biotin) to produce a biotin layer, and second with streptavidin, which bound the biotin layer to produce a streptaviden layer. Surface patterning was then accomplished by closing the button membranes and flowing a biotin-tagged DNA (expression template) over the non-masked area of the device. The biotin-tagged DNA bound to the non-masked portion of the streptaviden layer, producing a template layer in the non-masked areas only. The button membranes were deactivated and a biotinylated anti-penta-histidine antibody flowed over the surface. The biotinylated antibody bound the strepavidin surface in the previously non-masked portion of the substrate only.

Exemplary substrate modifying agents include, for example and not limitation, proteins (e.g., antibodies, receptors, fusion proteins), nucleic acids, glycans, lipids, carbohydrates and the like. The modifying agent may be tagged with a functional moiety such as biotin, avidin and the like. In some embodiments the modifying agent is a fusion protein comprising an affinity tag such as $His_6$, maltose binding protein, T7 tag, and the like. The substrate modifying agent may covalently react with the preexisting substrate or may noncovalently associate with the preexisting substrate.

As illustrated in the description above, in some embodiments the substrate is functionalized in several steps, including multiple rounds of differential surface patterning of the substrate, to produce layers. Thus, in some cases the substrate has previously been selectively modified. In certain embodiments, for example, the substrate modifying agent is biotinylated and the substrate (or a selected region thereof) has previously been modified to display an avidin. In some embodiments, substrate modifying agent comprises an antigen and the substrate (or a selected region thereof) has previously been modified to display an antibody that recognizes the antigen.

It will be understood that, as described in detail in the examples, washing and blocking steps are used as appropriate to remove unbound materials, block reactive moieties, etc. For example, the substrate modifying agent may be removed (e.g., by flushing the system with a wash buffer) or depleted (i.e., made unreactive or nonfunctional, e.g., by flushing the system with a compound that reacts with or modifies the modifying agent by reacting with or blocking a functional group).

Thus, in one aspect, the invention provides a method for selectively modifying the substrate in a unit cell of a microfluidic device by (i) masking a first portion of the substrate by contacting the first portion with a moveable element of the unit cell; (ii) contacting non-masked regions of the substrate with a substrate modifying agent; (iii) depleting or removing the substrate modifying agent; and (iv) unmasking the first portion of the substrate.

In some embodiments the substrates of only some of the unit cells of the device are modified or selectively modified.

Although the description above describes simultaneous actuation of all of the button membranes on the chip, the device can easily be programmed to actuate only subgroups of the button membranes, resulting in surface patterning of any desired complexity.

It will be recognized that, using common tagging and ligand-anti-ligand systems the substrate can be derivatized (either uniformly or with surface patterning) with a wide variety of molecules including, without limitation, polynucleotides (e.g., DNA and RNA), polypeptides, peptides, sugars, glycans, lipids, small molecules (e.g., synthetic or naturally occurring organic molecules MW<1000, such as drug candidates), toxins, individual atoms, etc. Molecules can be immobilized on the existing substrate using any number of methods including covalent or non-covalent interactions with the device support (e.g., glass, epoxy glass, protein-coated glass, plastic, etc.) or existing substrate, via ligand-antiligand systems (antibody-antigen, receptor-ligand, biotin-avidin, lectin-sugar, etc.) or other methods.

Mechanically Induced Trapping of Molecular Interactions (MITOMI)

In one aspect of the invention, actuation of the button (e.g., button membrane) may be used to, without limitation, physically trap surface bound molecules in the contact area, while expelling any unbound solvent and solute molecules. The trapped molecules may then be directly observed or tested against other compounds subsequently introduced into the system. In addition, fluid exchanges can be carried out without loss of bound material. The trapping of bound material protects it from subsequent wash and fluid exchange steps allowing background molecules to be removed and secondary reagents to be introduced into the system without disturbing the trapped material. MITOMI has several advantages over other currently available methods: it has a high intrinsic sensitivity and dynamic range, it allows the actual equilibrium binding constant to be observed since MITOMI literally freezes bound molecules at equilibrium without disturbing it. Protecting the bound molecules physically allows for additional fluidic steps to be performed without loss and thus results in the highest possible downstream signal.

Molecules (including molecular complexes) may be interrogated while trapped using optical or other methods as described below and/or known in the art. In one embodiment a transparent or semitransparent elastomeric material is used so that an optical signal from a trapped molecule can be detected from outside the device.

The contacting of the membrane with the surface preferably occurs in such a fashion that solvent and unbound solute molecules are not trapped between the membrane and the surface. In one embodiment initial contact of the membrane with the surface occurs medially and extends radially outward. Radial closure prevents solvent pockets from forming between the two interfaces and in effect creates zero dead-volume while preserving the equilibrium concentrations of the molecular interactions to be detected.

One element that can be optimized or MITOMI is closing velocity. As used herein, "closing velocity" refers to the velocity at which a free-standing membrane makes contact with the substrate. In the case of a button membrane, radial closing velocity refers to the speed at which the free-standing membrane expands contact with the surface starting from the central contact point which extends radially outwards at the radial closing velocity. The membrane closing velocity measured as the radial closing rate should be sufficiently fast to prevent molecules from dissociating while the membrane is being closed (see Example 3, infra). Generally, the velocity is sufficient that membrane when contacting the surface efficiently traps molecules between the two interfaces slowing down dissociational loss from the surface seen without membrane trapping by more than 2-3 orders of magnitude. Closing velocity is a function of the design of the trapping element and the actuation pressure (for trapping elements actuated by an increase in pressure in an actuation chamber). Closing velocity can be determined generally as described in Example 3, infra.

This method of physically trapping all surface bound molecules in the contact area, while expelling any unbound solvent and solute molecules allows highly sensitive secondary assays such as ELISAs to be performed on this microfluidic platform. Using this method it is possible to detect and quantify interactions between molecules, to detect specific binding interactions, and to determine bonding affinities, among other uses.

Subsequent to MITOMI (trapping) the trapping element can be deactuated and a change in state of the bound molecules detected. For example, it is possible to obtain the kinetic off-rate of the interactions under investigation by opening the membrane and allowing the bound material to dissociate while observing the rate of dissociation in real-time. Here the rate of loss of material directly returns $k_{off}$ of the interaction. Since now the $K_D$ and $k_{off}$ are known, $k_{on}$ may be computed and all kinetic parameters are obtained for the observed interaction. Using instrumentation capable of a simultaneously high time resolution while interrogating several square inches or more allows one to perform off-rate measurements in all 2400 unit cells. Likewise by taking advantage of MSLI one can arbitrarily address a large number of unit cells and perform off-rate assays with high time-resolution (limited only by the instrument taking the measurement) in sequence rather than in parallel.

One advantage of the present invention is that molecular interactions that are transient in nature and exhibit nanomolar to micromolar affinities, leading to rapid loss of bound material or little bound material in the first place can be detected and characterized.

In one aspect the invention provides a method comprising, in a unit cell of a microfluidic device, said unit cell comprising in a liquid environment (a) a substrate (b) a molecular complex comprising a first molecule immobilized in a contact area of the substrate, (c) a second molecule bound to the first molecule and thus indirectly bound to the substrate and (d) a movable element that upon actuation contacts the substrate in the contact area of the substrate; actuating the movable element causing it to contact the substrate in the contact area thereby physically trapping the first and second molecules bound to the substrate in the contact area while substantially expelling solvent and solute molecules. In one embodiment the movable element is an elastomeric trapping membrane.

In a related aspect the method involves the further step of de-actuating the movable element (e.g., reducing pressure in a membrane actuator chamber so that a button membrane retraces to it undeflected position). Usually the environment is changed prior to de-actuation of the movable element (e.g., any non-bound solute is removed by doing a fluid exchange step).

After actuating, and/or after deactuating, the movable element measurements can be made of, for example, total, solid phase and/or solution phase concentrations of the interacting molecules (e.g., surface bound protein and bound target DNA in the case of an immobilized DNA-binding protein interacting with a DNA molecule), and dissociation equilibrium constants or other values determined using standard methods.

Thus, in some embodiments the method further comprises detecting the complex of interacting molecules and/or detecting dissociation of the complex.

In some embodiments the effect of a third molecule on the interaction between the first immobilized molecule and second (bound or potentially bound) molecule is determined. In one approach, for example, method involves a) contacting the molecular complex is contacted with a third molecule; b) actuating the movable element causing it to contact the substrate in the contact area thereby physically trapping the first molecule and any second molecules bound to the first molecule substantially expelling solvent and unbound second molecules; and c) determining the d) the effect of the third molecule on association. In one approach, for example, method involves a) contacting the molecular complex with a third molecule; b) actuating the movable element causing it to contact the substrate in the contact area thereby physically trapping the first molecule and any second molecules bound to the first molecule substantially expelling solvent and unbound second molecules; c) de-actuating the movable element; and determining the d) the effect of the third molecule on dissociation of the complex. Optionally a fluid exchange step is carried out before de-actuating the movable element (i.e., the liquid environment is changed). The effect of the third element on the molecular interaction is determined by comparing values (e.g., the formation of the complex of interacting molecules; the dissociation of the complex, etc.) when the third molecule is present compared to values when the third molecule is absent. In some variations of this approach the effect of more than one additional molecule is determined (e.g., a third, fourth and fifth molecule).

It will be appreciated that information about the effect of an agent (third molecule) on an intermolecular interaction (between the first and second molecules) will be useful in screening for new therapeutic agents (drugs) that modulate (e.g., enhance or interfere with) intermolecular interactions.

In some embodiments the first molecule is a polypeptide (e.g., peptide, protein, receptor, antibody, etc.), nucleic acid, carbohydrate, lipid, glycan, or small molecule. "Small molecule" is used herein to refer to a composition, which has a molecular weight of less than about 5 kD. Small molecules can be nucleic acids, peptides, peptidomimetics, carbohydrates, or other organic or inorganic molecules.

In some embodiments the second molecule is a polypeptide (e.g., peptide, protein, receptor, antibody), nucleic acid, carbohydrate, lipid, glycan, or small molecule.

In some embodiments the third molecule is a polypeptide (e.g., peptide, protein, receptor, antibody), nucleic acid, carbohydrate, lipid, glycan, or small molecule.

In some embodiments, instead of adding a "third molecule" some other perturbation of the system is studied, such as a change in temperature, introduction of kinetic energy or pressure, etc. It will also be appreciated that although for the sake of simplicity reference has been made to a first, second and third "molecule," any or all of these molecules could actually be a molecular complex. Examples of molecular complexes include multi-subunit proteins or protein complexes (e.g., MHC complex, T cell receptor, polyketide synthase, microtubules, ribonucleoprotein complexes, proteasome, nuclear pore complex), nucleic acid complexes (e.g., triplex nucleic acids), etc.

In some embodiments, rather than measuring interactions amongst molecules one may measure the activity rate of an enzyme of other biological processes. In one example, in a first step the enzyme is trapped under the membrane, followed by fluid exchange introducing a solution containing a molecular substrate for the enzyme. Opening of the membrane will allow the enzymatic reaction to commence. The resulting modified substrate (e.g., a hydrolyzed substrate when the enzyme is a hydrolase) would be detected with standard art-known methods (including those described herein). Furthermore methods used in the detection of kinetics of interaction discussed infra may also be applied to measuring enzymatic rates.

Due to the simplicity of the approach the method may be highly integrated and parallelized. To date we have performed as many as 2400 distinct surface pattering reactions followed by MITOMIs on a single device in parallel. Furthermore an entire experiment is on the order of a few hours in duration, which makes it faster than most other methods of much lower degrees of parallelization. In some embodiment, the MITOMI methods described above are carried out in at least 100 unit cells of a microfluidic device, where each of the at least 100 unit cells contains a different first molecule and/or a different second molecule and/or optionally a different third molecule.

Detection of signal from unit cells will depend on the nature of the signal (fluorescent, radioactive, chemiluminescent, etc.) by the association, disassociation, reaction, etc. Most often optical methods are used. A variety of systems may be used including commercially available or modified microarray scanner (e.g., arrayWoRxe (Applied Precision), DNA microarray scanner (Axon Industries GenePix 4000B) and the like. Furthermore surface plasmon resonance may be used for detection of unlabeled molecular species by refractive index changes due to mass binding to the surface of the substrate. Additionally the product of chemical reactions (such as catalysis, synthesis etc.) may be detected with the above mentioned methods. When a molecular interaction is being detected typically, one or more of the molecules is labeled with a detectable molecule (e.g., a fluorescent element). Nucleic acids can easily be labeled during amplification or other synthesis steps using art-known methods. Proteins can be labeled (e.g., with a fluorescent dye or macromolecule) by, for example, building a chimeric protein making use of the various GFP variants or other fluorescent proteins, introducing a modified amino acid residue (e.g., residue specific incorporation via a modified tRNA charged with an amino acid linked to a dye), addition of an amino reactive fluorescent dye or quantum dot in the reaction mixture, or the like.

Use of MITOMI for Measuring Kinetic on and Off Rates

A trapping membrane may also be rapidly and repeatedly actuated and deactuated, similar to the mechanism used for pumping using a series of conventional monolithic valves. Rapid actuation and deactuation of the trapping membrane can be achieved with actuation rates on the order of 0.1-100 Hz, usually 0.1 to 20 Hz, often 1 to 10 Hz. Using rapid actuation of the trapping membrane can be used to control the time the detection area is either closed, open or both. This allows one for example to measure time dependent variables of molecular interactions such as the on and off rates of two or more molecules.

Measuring on rates with MITOMI. For illustration and not limitation, it is possible to measure the on-rate of a molecular reaction in the following way: The detection area is derivatized with Molecule A and protected by the trapping membrane in a closed state. A known concentration of Molecule B, which interacts with Molecule A, surround the detection area in solution. Opening the trapping membrane for x amount of time (where x is 0.1 to 100 seconds) will allow Molecules B to come into contact and interact with Molecule A. Subsequent closure of the trapping membrane will trap all Molecules B that were able to bind in time interval x. Consecutive repetitions of this approach allow one to collect y data points with time interval x (or any other time interval) and result in a curve describing the on rate of the system.

Measuring off-rates with MITOMI. A similar approach can be used for measuring off-rates. In this variation the detection area contains Molecule A as well as Molecule B in a complex. Repetitive opening of the trapping membrane will allow Molecule B to dissociate in x amount of time until the membrane is closed again. Consecutive measurements of this kind will allow one to measure the off-rate of the system.

These approaches have advantages over real-time off-rate measurements, as many thousands of molecules can be observed at the end of each time interval x since the state of the system is frozen by the trapping membrane. This allows for other detection mechanisms with limited time resolution (but good spatial resolution and area coverage) such as DNA array scanners to be used to quantify gain or loss of molecule B in the detection area. Using high frequency oscillations of the button membrane has the advantage that high time-resolution measurements of on and off-rates may be taken independently of the time-resolution of the instrument used for taking the measurement. The time-resolution in this case is solely limited by the actuation frequency of the trapping membrane.

Array Spotting

In some embodiments of the invention, reagents are introduced onto a unit cell chamber by "spotting." Usually reagents are introduced into the reagent chamber, but spotting may also be used to introduce reagents into the flow channel. By using array technology, a different reagent or different combinations of reagents can be added to each unit cell. For example, a DNA array can be used in which each unit cell contains a different DNA sequence. This process involves:

(1) obtaining
  (a) a solid support (e.g., an epoxy-coated glass slide), and
  (b) a partially fabricated MITOMI device lacking a substrate;

(2) spotting one or more reagents on the solid support in a microarray pattern thereby producing a microarray of the reagents on the solid support; and (3) aligning the microarray to the partially fabricated microfluidic device and adhering the two to produce a microfluidic device having a substrate formed from the solid support and oriented so that each spot (or predetermined group of spots) of the array is located in a unit cell chamber of the device. Array spotting, amplification and certain other processes described herein are described in copending application Ser. No. 11/698,802, "Programming Microfluidic Devices With Molecular Information", filed Jan. 26, 2007, incorporated herein by reference.

In one embodiment the solid support is an epoxy-functionalized glass slide, the partially fabricated microfluidic device is an elastomeric device formed from PDMS, and bonding occurs due to an attack of the electrophilic carbon of the epoxyde functional group by unreacted hydroxyl, alkoxyl or carboxyl groups of the PDMS. Bonding can be accelerated by heating the device to 40° C., or can be allowed to occur at room temperature. Other substrates include, for example and not for limitation, a tertiary layer of PDMS, unmodified glass, aldehyde surfaces, plasma treated surfaces etc.

Glass slides can be epoxy functionalized using 3-glycidoxypropyl trimethoxysilane, glycidoxypropyldimethoxymethylysilane, 3-glycidoxypropyldimethyl thoxyysilane or similar molecules (e.g., having an epoxy functional group linked to a silane group). In essence a silane molecule carrying a epoxyde functional group is either vapor deposited or absorbed in a liquid bath onto the glass surface where it the silane moiety covalently bonds to the glass surface. Vapor deposition simply involves vaporizing the above mentioned molecule (generally at room temperature as it is a volatile) in a small chamber to which the glass slides are added. In the liquid-dip process a roughly 1% solution of the above molecule in an organic solvent or mixture of organic solvent and water is used in which the slides are dipped until the surface has been coated with the above mentioned molecule. Epoxy coated slides are commercially available, e.g., CEL Associates (worldwideweb.cel-1.com), Telechem International (worldwideweb.arrayit.com), Xenopore Corp. (worldwideweb.xenopore.com).

The reagents deposited in the array can be any of a wide variety of compounds. In various embodiments the compound is selected from the following: DNA, RNA, proteins, peptides, antibodies, glycans, proteoglycans, receptors, cells, small organic molecules. Compounds that may be spotted include any soluble substance. Suspensions (e.g., small colloidal particles such as quantum dots, beads, bacterial cells and viral particles for example) can also be deposited and used to program the device, making the spotting method extremely useful for a plethora of applications, or small particles) that can be picked up and deposited by the arraying method used. The substrate in the area of deposition may be derivatized to bind or otherwise interact with the spotted reagent.

A wide variety of methods are known for producing arrays on a substrate such as a glass slide. See, for example, Heller, 2002, "DNA Microarray Technology: Devices, Systems, and Applications" *Ann Rev Biomed Eng* 4:129-53; Wingren & Borrebaeck, 2006, "Antibody microarrays: current status and key technological advances" *OMICS* 10:411-27; Oh et al., 2006, "Surface modification for DNA and protein microarrays" *OMICS* 10:327-43; Uttamchandani et al., 2006, "Protein and small molecule microarrays: powerful tools for high-throughput proteomics" *Mol Biosyst.* 2:58-68; and Uttamchandani et al., 2005, "Small molecule microarrays: recent advances and applications" *Curr Opin Chem Biol.* 9:4-13, each of which is incorporated herein by reference.

Technologies for forming microarrays include both contact and non-contact printing technologies. One example is the PixSys 5500 motion control system from Cartesian Technologies (Irvine, Calif.) fitted with the Stealth Micro-spotting printhead from TeleChem (Sunnyvale, Calif.). Contact printing technologies include mechanical devices using solid pins, split pins, tweezers, micro-spotting pins and pin and ring. Contact printing technologies are available commercially from a number of vendors including BioRobotics (Boston, Mass.), Genetix (Christchurch, United Kingdom), Incyte (Palo Alto, Calif.), Genetic MicroSystems (Santa Clara, Calif.), Affymetrix (Santa Clara, Calif.), Synteni (Fremont, Calif.), Cartesian Technologies (Irvine, Calif.) and others. Non-contact printing technologies include "ink-jetting" type devices such as those that employ piezoelectrics, bubble-jets, micro-solenoid valves, syringe pumps and the like. Commercial vendors of non-contact printing technologies include Packard Instruments (Meriden, Conn.), Agilent (Palo Alto, Calif.), Rosetta (Kirkland, Wash.), Cartesian Technologies (Irvine, Calif.), Protogene (Palo Alto, Calif.) and others. Both contact and non-contact devices can be used on either home-made or commercial devices capable of three-dimensional movement. Motion control devices from Engineering Services Incorporated (Toronto, Canada), Intelligent Automation Systems (Cambridge, Mass.), GeneMachines (San Carlos, Calif.), Cartesian Technologies (Irvine, Calif.), Genetix (Christchurch, United Kingdom), and others would also be suitable for manufacturing microarrays according to the present invention.

The amount of compound required will depend on the particular nature of the assay, but, for proteins and nucleic acids, attomole amounts usually are sufficient.

The size of the microarray is typically about 1.0-2.0 cm$^2$ but may vary over a large range. The array pattern is not critical and can be optimized for a particular device or assay. A typical spot diameter is about 100 um (usually in the range 50-100 um, depending on the method of spotting), with spots placed at a center-to-center spacing of about 140 um (usually in the range 200-1000 um, or separating spots by at least about 10 um), to allow each spot to form at a distinct and separate location on the substrate. In one embodiment, compounds are spotted as microarrays with a column pitch of about of 563 µm and row pitch of about 281 µm.

In making an array, a small volume of a solution containing reagents is usually deposited, and the solvent allowed to evaporate leaving a desiccated reagent. The desiccated reagent spots are thus introduced into the device and may be re-solvated by introducing liquid through the flow channel network. A carrier may be introduced to facilitate re-solvation of the reagents, for example reagents may be co-spotted with a 1%-2% BSA solution. BSA may be added to the solution before spotting or BSA can be co-spotted (e.g., under a spot of reagent). The co-deposited BSA also aids in the visualization of the spots useful for the manual alignment of the array to the microfluidic chambers. Other additives such as other proteins, NaCl or other salts, PEG and other larger organic molecules may also be used as carriers.

Since all the spots are ultimately segregated on the microfluidic device by specific channel geometry and active valves, it is possible to make efficient use of arrays that are more complex than conventional arrays. Two approaches—"co-multispotting" and "neighbor spotting"—are especially useful for introducing more than one solution to the same vicinity, creating complex multiplexed arrays on a MITOMI chip.

In "co-multispotting" two or more different reagent-containing solutions are deposited on top of one another in sequential rounds of spotting, so that several different components are located in the same place on the array. See, e.g., FIG. 7, Panel B. This figure illustrates cospotting to generate 3-solution combinations of 3 pairs of solutions (Pair 1=A and B; Pair 2=1 and 2 and Pair 3=alpha and beta). If any given spot contains only one member of a pair, the total number of possible combinations is $2^3$=8, or. In one embodiment the array is generated by spotting members of the first pair in columns, followed by a second round of spotting of the same or different solutions across rows. In this example, the first two rounds represent a standard two dimensional array of dimensions m×n where m is the number of columns and n the number of rows of the array. Printing of a three dimensional array of shape m×n×o can be accomplished by spotting o copies of the two-dimensional array m×n. So in the case shown in Panel B of FIG. 7 a three-dimensional array of shape m=n=o=2 is spotted on a two dimensional substrate. Likewise any array of higher dimensionality can be printed using the same technique. The deposits of solution A and B spotted in the same round may be spotted in sequence without the need of a wash step between duplicate spots. For any subsequent round of spotting it is preferred, if pins are used for deposit, to wash between every deposited spot due to possible contamination of the pin from the previously deposited spot. Co-multispotting is extremely space efficient since it requires the same area as a standard array, and spots may be spaced with a minimal pitch merely dictated by the pin, spotting robot and fluidic layout to which the array is being aligned. Co-multi-spotting can also be used to increase reagent concentration per spot by multispotting the same solution several times on the same spot, each time delivering more reagent to the amount already present on the slide.

A second approach to multiplexing by spot deposition is the method of "neighbor-multispotting" depicted in Panel C of FIG. 7. Here instead of spotting the various solutions directly on top of one another, they are spotted immediately adjacent to one another. The total footprint of the neighboring spots is designed to fit into a single reagent chamber of the MITOMI device, and each group of spots is ultimately segregated on the device. Upon resolution the spotted reagents are allowed to mix by passive diffusion. This approach has the disadvantage of requiring a larger footprint per spot then the co-multispotting method. However, in some applications this disadvantage is outweighed by the elimination of cross-contamination between spotting since a pin, for example, does not touch a previously deposited spot. Eliminating cross-contamination in this fashion allows for significant time savings by reducing the number of wash steps required. Like co-multispotting, neighbor multispotting can be used to increase reagent concentration by depositing neighboring spots containing the same reagent. Neighbor multispotting typically results in two or more reagents in distinct spots in an area of not more than 1 $mm^2$, sometimes in the range of 0.1 to 0.5 $mm^2$, 0.2-0.5 $mm^2$, 100 $microns^2$-1 mm2 ($um^2$), 100 $um^2$-200 $um^2$.

In one aspect the invention provides a method of fabricating a microfluidic device by i) positioning an elastomeric block comprising a plurality of chamber recesses and a solid support comprising a microarray of discrete reagent-containing regions so as to align each reagent-containing region with a recess; ii) adhering the block to the solid support so as to produce a plurality of chambers containing reagents. A device made from a nonelastomeric material can be aligned with a substrate in essentially the same manner. In one embodiment the microarray has 10 to 5,000 reagent-containing regions, more often 100 to 2400 reagent-containing regions. In one embodiment each reagent containing region contains two or more different reagents. In one embodiment each reagent containing region contains 1, 2 or 3 or more discrete subregions, each containing a different reagent. In one embodiment the microarray has a density of about 100 or more discrete regions per $cm^2$ or about 1000 or more discrete regions per $cm^2$. In one embodiment the microarray contains 10 or more different reagents, more often 100 or more different reagents, and often 500 or more different reagents.

In one aspect the invention provides a method of fabricating a microfluidic device by i) depositing reagents on a solid support to produce a microarray of discrete reagent-containing regions; ii) positioning an elastomeric block comprising a plurality of chamber recesses and the reagent-containing regions so as to align each reagent-containing region with a recess; iii) adhering the block to the solid support so as to produce a plurality of chambers containing reagents. In one embodiment the reagents are deposited by contact printing. In one embodiment the reagents are deposited by non-contact printing. In one embodiment the reagents are deposited on the solid support robotically. In one embodiment the microarray has a density of about 100 or more discrete regions (corresponding to the contents of a single chamber) per $cm^2$. In one embodiment the microarray has a density of about 1000 or more discrete regions per $cm^2$.

In one aspect the invention provides a microfluidic device with at least 100 unit cells, each unit cell having a first microfluidic chamber having a substrate, and a reagent in dry form disposed on a reagent-containing region of the substrate where at least 100 unit cells of the device each contains a different reagent, different amounts of a reagent, or a different combination of reagents.

In Situ Transcription and Translation

As described in the Examples, in vitro transcription and/or translation can be carried out in unit cells of the MITOMI device. The resulting products (nucleic acid or protein) can serve any of a variety of functions including, for illustration and not limitation: enzymatic (e.g., catalyses a reaction in the unit cell to generate a product used in analysis); binding (e.g., the product can act as a ligand or antiligand in an analytical or screening assay, as illustrated in the examples); modulating (e.g., the effect of the product on a molecular interaction between other molecules in the unit cell can be determined) and other functions.

In one embodiment, as described in the examples, in vitro transcription and translation (ITT) occurs when the unit cell is fluidically isolated from other unit cells and/or when the detection area is fluidically isolated from reagent chambers. ITT can be used to produce analytes or reactants in a unit cell chamber or flow channel.

In one embodiment the expression template (the nucleic acid from which transcripts are made) is immobilized. Preparation and use of expression vectors and linear expression templates is well known. In one embodiment the expression template is produced using a two-step amplification as described in copending application No. 60/762,344, incorporated herein by reference. In one embodiment the template is immobilized on the unit cell substrate (e.g., optionally using a tag such as biotin) and a wheat germ extract (or other transcription/translation system) is added subsequently. In another embodiment, the transcription/translation system is added together with the template and distributed to individual unit cells, which are then sealed and protein synthesis allowed to proceed. For example, in one embodiment, after surface patterning the device is loaded with wheat germ based ITT mixture containing linear DNA template coding for a protein to be synthesized and each unit cell is isolated by closing a set of micromechanical valves. The device is incubated at 30° C. for 90 min to complete protein synthesis.

In one embodiment, multiple different proteins are produced in situ in the same unit cell. These multiple proteins may be variants of a base sequence, may interact with each other or compete for interaction with another molecule, may function in a common synthetic or metabolic pathway, may have another relationship or may be unrelated.

Exemplary Analysis

For illustration a hypothetical analysis is presented in this section. It should be understood that this description is simply to illustrate certain aspects of the invention and is not intended to limit the invention in any way.

| Step | |
|---|---|
| 1 | Prepare linear expression template ("target DNA") of gene encoding a ligand ("target protein"). |
| 2 | Spot plain epoxy support with 2400 unique spots of a peptide library, in which at least some of the peptides are believed to be an anti-ligand for the target protein, to form a microarray. The peptides are tagged with a fluorophore. |
| 3 | Align and adhere an elastomeric block comprising a plurality of chamber recesses so as to align each reagent-containing region with a recess corresponding to a "reagent |

| Step | |
|---|---|
| | chamber," thereby producing a microfluidic device containing unit cells having (i) a reagent chamber in which target peptide is deposited on the substrate; (ii) a flow channel with a detection area in fluidic communication with the reagent chamber and with detection areas of two adjacent unit cells; (iii) valves between the detection areas and between the detection area and the reagent chamber (allowing the reagent chamber and detection area to be isolated by closing the valves); and a membrane actuator chamber positioned over the detection area and separated from it by a thin deflectable elastomeric membrane. |
| 4. | Fluidically isolate the reagent chamber by closing the appropriate valve. |
| 5. | Differentially derivatize the substrate of the detection area, so that the detection area, and no other area of the substrate, has an stepavidin substrate. |
| 6. | Introduce a biotinylated penta-histidine tagged antibody against the target protein, which is immobilized in the detection area. |
| 7. | Introduce ITT containing the target DNA (linear template) into the detection area and close valves to isolate chamber. The target protein is synthesized and then immobilized by binding to antibody. |
| 8. | Open valve between detection area and reagent chamber; allow peptides to solvate and bind the immobilized target protein. |
| 9. | Actuate the button membrane to mechanically trap any peptide bound to immobilized target protein molecular interactions taking place on the surface allowing all solution phase molecules to be washed away without loss of surface bound material. |
| 10. | Fluorescent scan of the device to detect quantities of trapped molecules, in solution molecules. |
| 11. | Remove any unbound (solution phase) peptides by flushing chamber with buffer. |
| 12. | De-actuate button membrane and detect bound peptide (showing interaction) |
| 13. | Measure rate of dissociation of peptide from target protein. |

EXAMPLES

Example 1

Surface Patterning and MITOMI

This example describes a prototypical MITOMI device. A device was fabricated, a protein-based surface chemistry for protein binding was generated, and protein capture and MITOMI were carried out.

Additionally the effect of varying chamber diameters on the effective surface contacting area was also studied.
Experimental Methods
A) Flow and Control Mold Manufacturing Two 3-inch silicone wafers were treated with hydroxymethyl silane (HMDS, Sigma) for 2 minutes followed by spin coating with the positive tone photoresist SPR 220-7.0 (Rohm & Haas) in two consecutive spin steps. The first spin step was performed at 500 rpm for 5 seconds followed by 3000 rpm for 60 seconds. The wafers were then soft-baked at 105° C. for 90 seconds. The flow and control patterns were transferred to the molds using two separate transparencies printed with their respective patterns at 20,000 dpi (CadArt). Exposure was done at 365 nm on a MA-6 Mask aligner (Karl Suss) for 15 seconds. Subsequently the molds were developed in a 5:1 bath of distilled water and 2401 developer (Shipley) respectively until the channel patterns were visible and any excess background removed.
B) Chip Fabrication For the control layer 36 grams of a 5:1 ratio of Part A to Part B Sylgard (DowCorning) were mixed together in a Hybrid mixer (Thinky Corporation) for 1 minute followed by degassing for 2 minutes. The mixture was then poured on top of the control layer mold sitting in a Petri dish lined with aluminum foil and further degassed in a vacuum chamber for roughly 5 minutes. The flow layer consisted of 31.5 grams of a 20:1 mixture of part A to part B Sylgard, which was also mixed for 1 minute and degassed for 2 minutes in the hybrid mixer. The flow layer mixture was then spun onto the flow layer mold at 3000 rpm for 30 seconds with a 15 second up-ramp and no down-ramp. Both layers where cured at 80° C. for 30 minutes after which the control layer was cut and removed from the control layer mold. Access holes were punched with a 21 gauge manual puncher. The control layer was then manually aligned to the flow layer and the two where bonded together at 80° C. for 2-3 hours. Finally the monolithic device was peeled of the flow layer mold and access holes to the flow layer were punched with the same puncher as before.

The finished chip was placed on an epoxy slide (CEL Associates) previously coated with bovine serum albumin (BSA, Sigma) by submerging the slide in a 2% BSA phosphate buffered saline (PBS) solution for 2 hours followed by a dH2O wash and dying under a stream of Nitrogen.
C) Preparation of Control Lines and Protection of Surface All the control lines of the device were connected to tubes filled with distilled water and actuated at 5 psi until all control channels were dead-end filled with liquid. During the experiment, control lines where actuated at a pressure of 15 psi.
D) Activation of BSA Surface Layer Initial activation of the BSA surface layer was performed by introducing 4.4 mM Biotinoyl-epsilon-aminocaproic acid-N-hydroxysuccinimide ester (NHS-ester biotin, Roche) in a 10% solution of dimethyl formamide (DMF) in PBS at a constant flow rate at 5 psi for 48 minutes. This was followed by a 10 minute long wash with PBS. The surface was then coated with streptavidin (Roche) by flowing a 500 μg/mL streptavidin (Roche) PBS solution into the device for 23 minutes, followed by a 5 minute PBS wash.

The button membranes were closed and washing continued for an additional 5 minutes. Once washing was complete the non-protected area of the device was derivatized with a PCR derived linear expression template coding for MAX isoform A N-6×His which was flowed through the serpentine channel for 55 minutes. The expression template was covalently coupled on the 5' end to a Cy3 fluorophore and on the 3' end to biotin. Any unbound or loosely bound template was removed in a 8 minute long PBS wash step.

Once the channels were cleared of residual templates, a 1:1 solution of biotinylated anti-penta-histidine antibody (Qiagen) in 2% BSA PBS was introduced into the serpentine for 5 minutes before de-actuating the button membrane and allowing the antibody to coat the now accessible streptavidin surface for 10 minutes under constant flow. This was again followed by a 8 minute long PBS wash.

In order to synthesize protein in situ using the previously deposited linear DNA, a standard wheat germ based in vitro transcription/translation reaction (Promega) spiked with 1 µL tRNALys-bodipy-fl and 1 µL of a 1/10 dilution of a dsDNA oligomer containing a transcription factor binding sequence, was introduced into the serpentine for 9 minutes. Each unit cell was then segregated and the entire device was incubated for roughly 2 hours on a 31.9° C. warm hotplate.

The button membrane was then closed one more time trapping any surface bound protein-DNA complexes and the serpentine flushed with PBS for 19 minutes.

FIG. 2 shows a schematic of the surface chemistry that was generated on the device as well as the process of protein synthesis, capture and MITOMI. Colored boxes indicated fluorescently labeled molecules, green=fluorescein, yellow=Cy3 and red=Cy5. Panel A shows the final surface chemistry just prior to introduction of the in vitro transcription/translation reagents. Each grey block represents a monolayer consisting of the indicated molecule. Panel B describes the process of protein synthesis using the deposited linear expression templates. The synthesized MAX isoA protein diffuses to the antibody coated surface and is pulled down via its N-terminal 6× Histidine tag. The free Ebox DNA molecules, introduced with the ITT mix, are recognized by MAX iso A and likewise pulled down to the surface. In Panel C MITOMI is performed by closure of the button membrane, trapping any bound material and expunging any unbound material. This schematic corresponds to the image in FIG. 3, panel B. Panel D shows the final state of the device after the last PBS wash removing any unbound material from the adjacent material. This schematic corresponds to the image in FIG. 3, Panel B.

Results

Figure 3A:
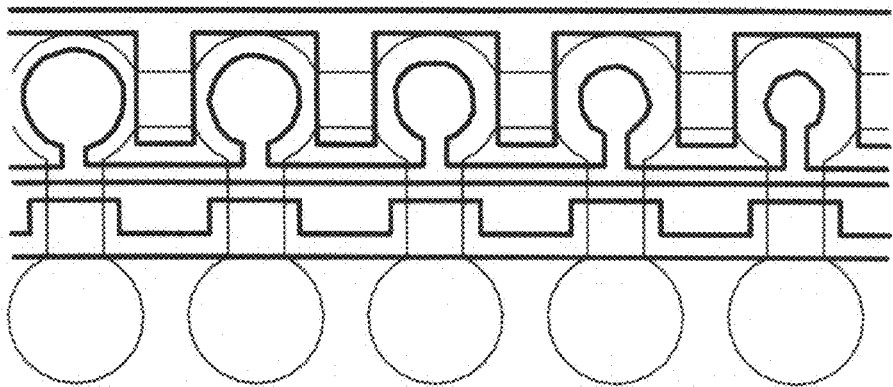
Figure 3B:
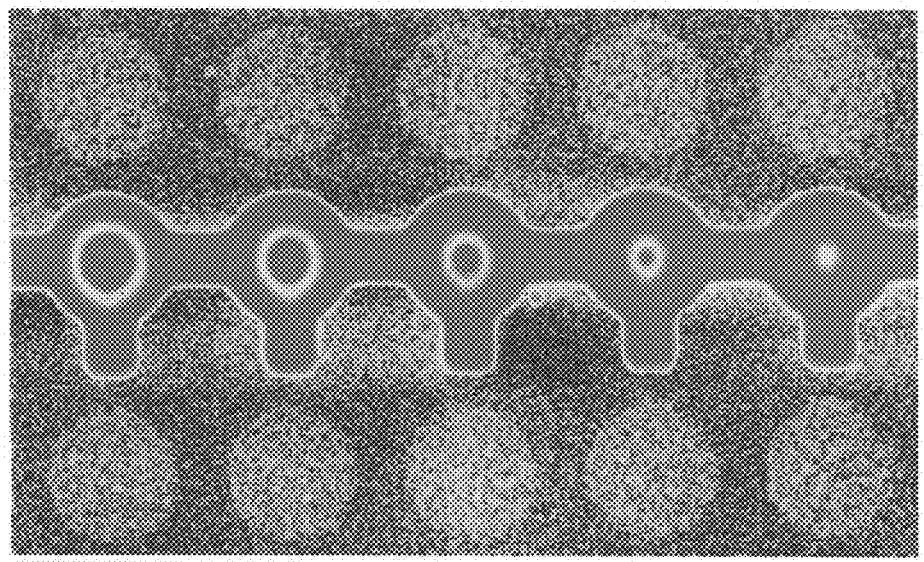
FIG. 3B).
Figure 3C:
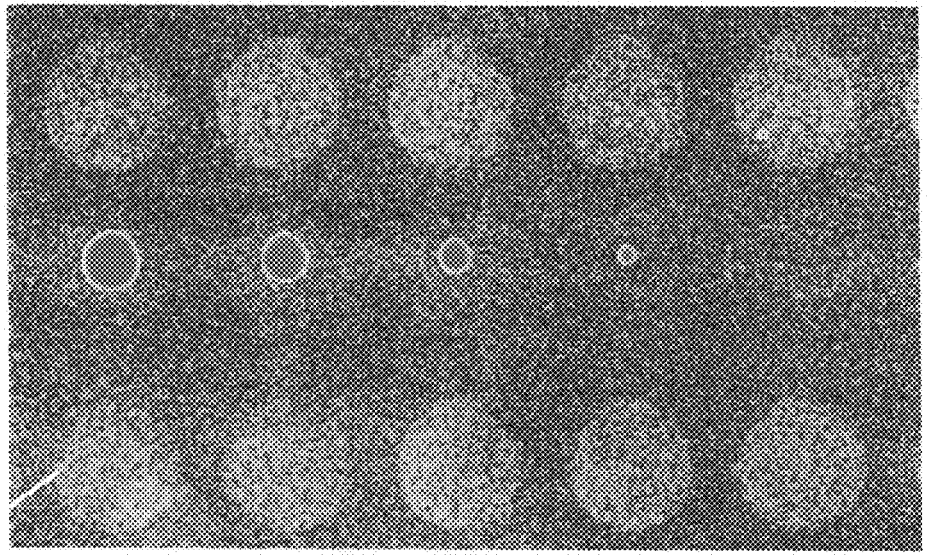
FIG. 3C).
Figure 4:
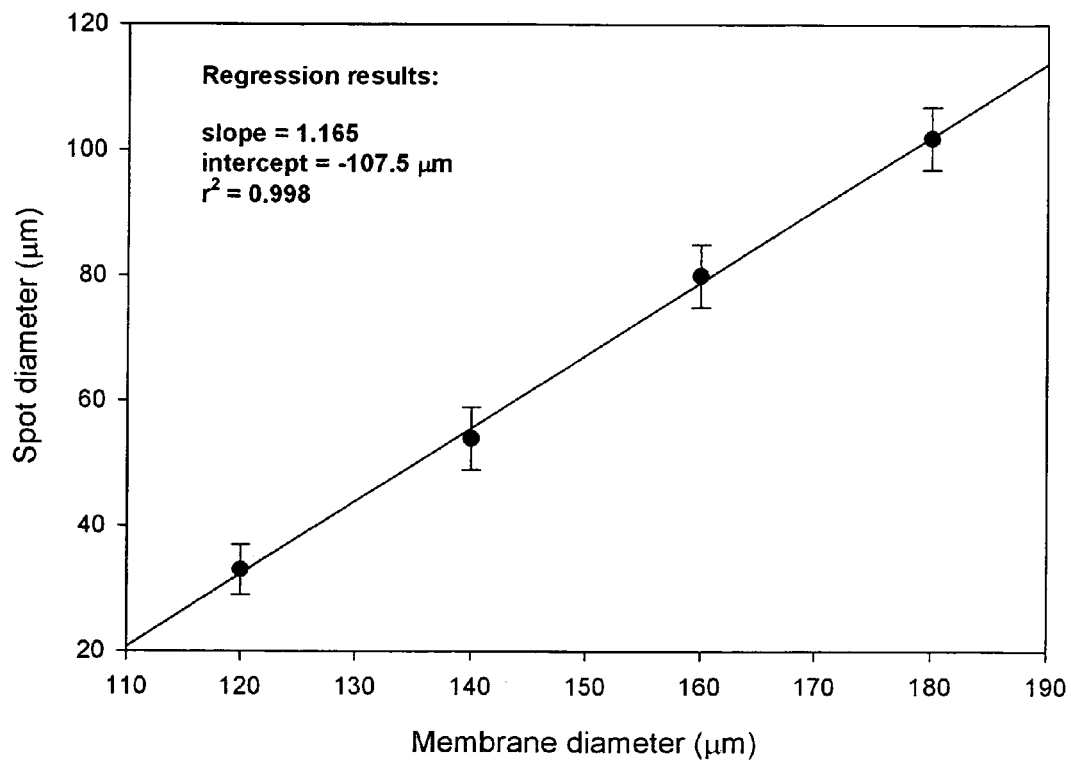
FIG. 4 shows the relationship of spot size dependence and membrane diameter.

FIG. 3 summarizes the results of the experiment. Panel A shows an AutoCad schematic of a subsection of the device used in this experiment. Flow layers are outlined by blue lines and the control layer situated on top of the flow layer is outlined in red. Note the red circles of varying diameter. These constitute the chambers creating the button membrane. In Panel B a section of a scan taken with a modified DNA array scanner (ArrayWoRxE, Applied Precision) is shown. The image was acquired in the Cy5 band, and thus shows the relative fluorescent intensity of the Ebox DNA that was spiked into the ITT reaction. The intensity scales (in grey scale or in false colors from green to red, with green being the lowest concentration and red the highest.) It can be seen that only the flow channel but not the chamber show signal, which is to be expected since the chambers were not filled and remained empty. Furthermore it is apparent that each unit cell contains a concentric ring of low intensity of varying diameter, with a high intensity bull's-eye. This pattern stems from the button membrane closure and MITOMI and is indicative of two things. First the bright bull's-eye originates exclusively from surface bound Ebox-DNA specifically bound by MAX iso A. Secondly, the surrounding low intensity ring indicates that no non-specific trapping of molecules occurs. The low intensity ring is seen because the button membrane was closed at a higher pressure than used originally to protect the surface from derivatization with linear expression template. Meaning that the membrane now contacts a larger surface area, but Ebox-DNA is only trapped where it was pulled down by MAX isoA and not where it can only make non-specific interactions with the surface bound linear-expression template. Panel C shows the same area of the device after a PBS wash step indicating that fluid exchange may be performed without loss of trapped material. It should be noted that the MAX iso A-Ebox DNA interaction has a high intrinsic $k_{off}$ rate on the order of 0.2 sec−1 and a overall affinity in the low nanomolar range. The extent of non-specific trapping of solute material by closure of the button membrane is described in further detail in Example 2, infra. In order to assess how contact diameter depends on chamber size we designed a device that contains chambers of varying sizes ranging from 180 µm down to 80 µm in 20 µm steps. Initial actuation was tested at varying pressures to understand what minimal pressure is required to put each of the membranes into contact with the surface. The results are summarized in Table 1 and show that all tested membranes may be deflected and closed and that the actuation pressures fall within reasonable bounds of up to 20 psi. Additionally the dependence on the membrane-surface contact area as a function of chamber diameter at a constant closing pressure of 15 psi was also determined by plotting the resulting spot diameter as a function of chamber diameter (FIG. 4). The results show that the resulting contact surface is directly and linearly dependent on chamber diameter with a slope close to 1. Therefore the actual area to be contacted can easily be predicted and modulated by increasing the chamber diameter, closing pressure as well as flow channel height. Where the latter two parameters will most likely only affect the intercept of the line and not the slope.

TABLE 1

Spot size dependence and uniformity

| Membrane diameter (µm) | Initial closing pressure (psi) | Spot diameter at 15 psi (µm) | Std. dev. (µm) |
|---|---|---|---|
| 180 | 6.5 | 102 | 5 |
| 160 | 6.5 | 80 | 5 |
| 140 | 6.5 | 54 | 5 |
| 120 | 7.5 | 33 | 4 |
| 100 | 19 | — | — |
| 80 | 19 | — | — |

Example 2

Establishing Detection Sensitivity Levels

Figure 5:
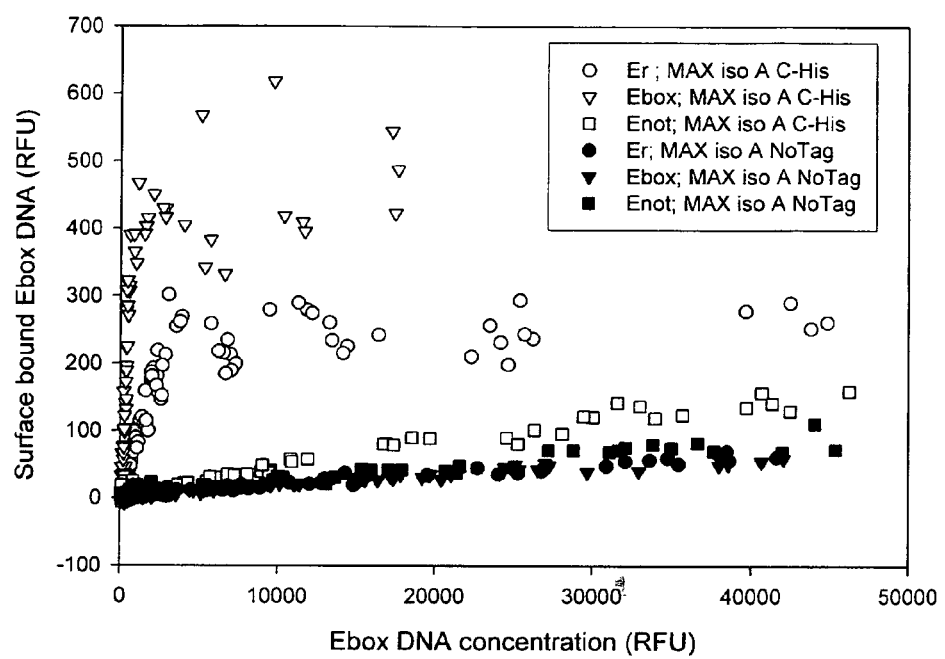
FIG. 5 shows differences in apparent pull-down and trapping of free Ebox-DNA carrying various recognition sequences by MAX iso A with a 6×His tag (open symbols) and non-tagged (closed symbols).

In order to address the question what the lower detection bounds are for this system we determined at what concentrations non-specific trapping occurs. To do so a device similar to the one described in Example 1 was used. We tested three different Ebox-DNA sequences: Ebox, Er and Enot containing the following E-box binding sequences respectively: CACGTG, CAGGTG and TGATGC. MAX iso A binds the Ebox sequence with a strength in the nanomolar range with decreasing affinities for Er and Enot. Enot binds only non-specifically via interactions with the phosphate backbone and its' affinity is considered negligible falling into the µM regime and considered non-specific. These three sequences when tested in our system return the approximate affinities of 166 nM, 1.3 µM and 23 µM for Ebox, Er and Enot respectively when bound to the surface by a C-terminally 6× Histidine tagged MAX iso A version (FIG. 5). More importantly when MAX iso A without an affinity tag is used all measured affinities drop to roughly 50 µM.

In this experiment 50 µM was the value where non-specific binding dominates in this system. It is noteworthy that using MITOMI it is possible to resolve binding differences between non-specific binding due to DNA phosphate backbone interactions as was the case with Enot binding to MAX iso A C-His, which using standard methods would have been lost in the overall non-specific binding observed with tag-less versions of MAXiso A. Affinities in biological systems can be as low as a few dozen μM, which we are still able to capture in our system. Any affinities lower then the ones reported herein can be considered non-specific and thus likely not important in biological processes. Our system also has been shown to have a dynamic range of at least two orders of magnitude, ranging from about 50 μM to roughly 200 μM. Higher affinities should also be detectable, since they are generally easier to detect, extending the dynamic range by at least another order or two.

In summary we have developed a method for the highly-parallel and sensitive detection of molecular interactions that may be applied to a broad range of interactions and does not require extensive optical setups for detection. Detection sensitivity and dynamic range cover all biologically relevant affinities making MITOMI broadly applicable for the detection of molecular interactions.

Example 3

A Microfluidic Platform to Measure Low Affinity Interactions Enables Comprehensive Characterization of Transcription Factor Binding Energy Landscapes and Prediction of Gene Regulation This example describes the use of MITOMI to map the binding energy landscapes of four eukaryotic transcription factors (TFs) belonging to the basic helix-loop-helix (bHLH) family by collecting over 41,000 individual data points from more than 17 devices and covering titrations over 464 target DNA sequences. These binding energy topographies allowed us to 1) predict in vivo function for two yeast TFs, 2) make a comprehensive test of the base additivity assumption, and 3) test the hypothesis that the basic region alone determines binding specificity of bHLH TFs. bHLH motifs represent the third largest TF family in eukaryotes and regulate a wide variety of cellular functions ranging from cell proliferation and development to metabolism. Information in this Example is found in Maerkl S J and Quake S R, 2007, "A systems approach to measuring the binding energy landscapes of transcription factors" *Science* 315:233-7, incorporated herein by reference.

We studied isoforms A and B of the human TF MAX, which together with other bHLH members play a role in cellular proliferation and many cancers. We also studied the yeast TFs Pho4p and Cbf1p; the former regulates phosphate metabolism, while the latter regulates methionine synthesis as well as chromosome segregation, serving a structural role in the kinetochore. bHLH TFs generally bind to a consensus sequence of 5'-CANNTG-3' called "enhancer box" (E-box), which was later found to be the second most conserved motif in higher eukaryotes. Members of the bHLH family show mid to low nanomolar DNA binding affinities and have off-rates above $10^{-2}$ $s^{-1}$ for their consensus sequences with orders of magnitude higher off-rates for non consensus sequences. This transience makes the use of conventional microarrays impractical.

Overview

The TF binding energy topographies were measured with highly integrated microfluidic (MITOMI) devices (Thorsen et al., 2002, *Science* 298:580) containing 2400 independent unit cell experiments (FIGS. 6A and 6B). Each device is controlled by 7,233 valves fabricated by multilayer soft lithography (MSL) (Unger et al., 2000, Science 288:113) and programmed with a 2,400 spot DNA microarray (Shena et al., 1995, *Science* 270:467). The 2,400 chambers are arranged into 24 rows addressed via a resistance equalizer (FIG. 6A); this ensures that flow velocities are equal across all rows, resulting in uniform surface derivatization and TF deposition. (Also see WO 2006/071470 describing a distribution manifold.)

The device was designed in AutoCAD2004 (Autodesk, Inc.) and each layer reproduced as a chrome mask at 20,000 dpi (Fineline-Imaging). Flow molds were fabricated on 3" silicon wafers (Silicon Quest International) coated with hexamethyidisilazane (HMDS) in a vapour bath for 2 min. The wafers were then spin coated with SPR 220-7 (Shipley) initially at 500 rpm for 5 s followed by 4000 rpm for 60 s yielding a substrate height of around 6-7 μm. The molds were baked at 105° C. for 90 s followed by a 15 s I-line exposure on a MA6 contact mask aligner (Karl Suss). Next the molds were developed with 1:5 2401 developer (Microposit) in dH2O. Finally the molds were annealed at 120° C. for 20 min. Control molds were fabricated on 3" silicon wafers by spin coating SU-8 2025 (MicroChem) at 2700 rpm for 80 s followed by a 65° C. bake for 2 min, 95° C. for 5 min and a final step of 65° C. for 2 min. The wafers were then exposed for 10 s on the I-line, followed by a post-exposure bake series of 65° C. for 2 min, 95° C. for 12 min and 65° C. for 2 min. The wafers were then developed in SU-8 developer for 90 s followed by an acetone and isopropanol wash. One wafer from each control and flow wafer set was selected and used for all subsequent microfluidic device fabrication. The microfluidic devices were fabricated essentially as described previously (Thorsen et al, 2002, Science 298:580).

a) Target DNA Synthesis

We synthesized libraries of Cy5 labeled target DNA sequences which comprehensively cover the E-box motif and flanking bases by permuting up to four bases at a time.

All small dsDNA oligos serving as targets for transcription factor binding were synthesized by isothermal primer extension in a reaction containing 6.7 μM 5'CompCy5, 10 μM library primer, 1 mM of each dNTP, 5 units Klenow fragment (3'→5' exo-), 1 mM dithiothreitol 50 mM NaCl, 10 mM MgCl2 and 10 mM Tris-HCl, pH7.9 in a final volume of 30 μL. All reactions were incubated at 37° C. for 1 h followed by 20 min at 72° C. and a final annealing gradient down to 30° C. at a rate of 0.1° C. sec−1. We added 70 μL of a 0.5% BSA dH2O solution to each reaction and transferred the entire volume to a 384 well plate in which a 6 fold dilution series was established with final concentrations of 5'CompCy5 of 2 μM, 600 nM, 180 nM, 54 nM, 16 nM and 5 nM.

b) DNA Arraying and Device Alignment

Dilution series for each target DNA sequence were spotted as microarrays with a column and row pitch of 563 μm and 281 μm, respectively. These arrays were used to program the microfluidic devices by aligning each spot to a unit cell.

Programming devices with microarrays simplifies the microfluidic infrastructure and increases unit cell density. The use of microarrays for device programming is highly modular as any soluble substance or suspension may be arrayed and it provides an elegant and efficient solution to the world to chip interface problem. Approximately attomoles of DNA and TF are required for each data point.

All target sequences were spotted with an OmniGrid Micro (GeneMachines) microarrayer using a CMP3B pin (TeleChem International, Inc.) for delivery onto epoxy coated glass substrates (CEL Associates). Each sample solution contained 1% BSA in dH2O to prevent covalent linkage of the target DNA to the epoxy functional groups as well as for visualization during alignment. After spotting the arrays were quality controlled on a GenePix4000b (Molecular Devices). The arrays could then be stored in the dark at room temperature until aligned to a microfluidic device. Device alignment was done by hand on a SMZ1500 (Nikon) stereoscope and bonded overnight in the dark on a heated plate at 40° C.

c) Linear Template Synthesis

To avoid time consuming cloning and protein synthesis/purification steps, the TFs are synthesized in situ via wheat germ based in vitro transcription/translation (ITT). We designed a two-step PCR method that generates linear expression ready templates directly from yeast genomic DNA or cDNA clones. This approach allowed us to not only rapidly screen new TFs, but also to easily create and test structural chimeras.

Figure 9A:
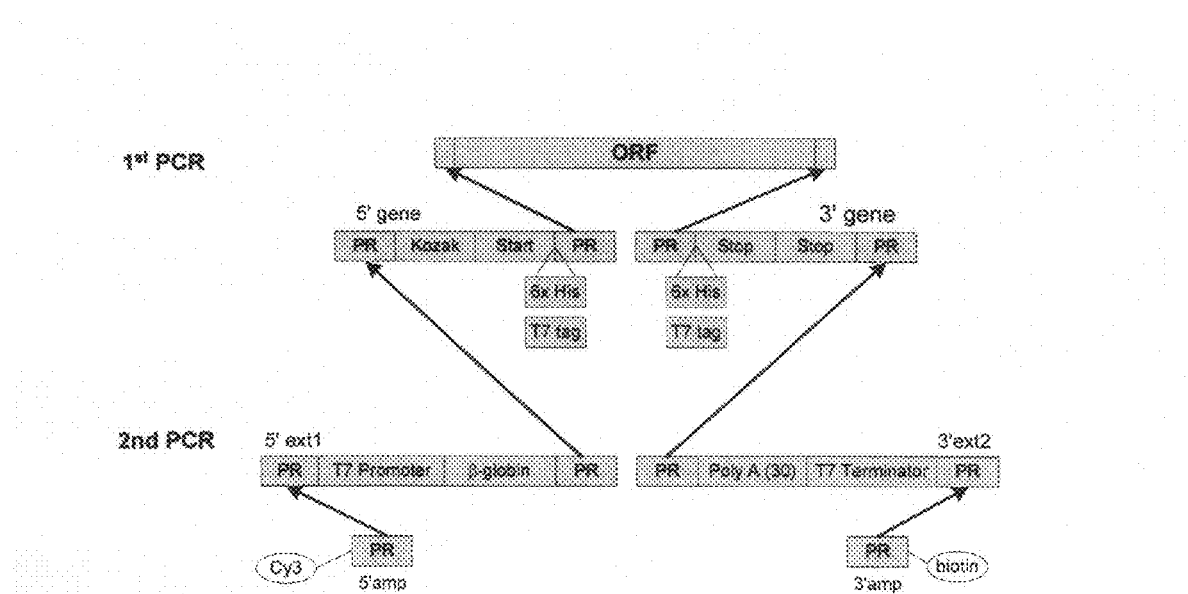
FIG. 9A shows a two step PCR method for generating linear expression templates.
Figure 9B:
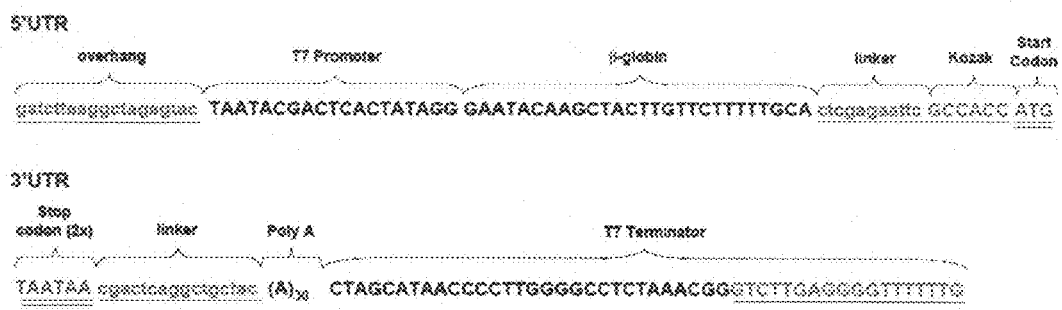
FIG. 9B shows the 5' and 3' UTR sequences (SEQ ID NOS:1 and 2, respectively) added by the 2 step PCR method. All regions are annotated and all priming sequences are in red. The start and stop codons are colored green. The entire 5' and 3' UTRs are added by the 5' extension and 3' extension primers respectively except for the start and stop codons.

Linear expression templates were generated by a two step PCR method (FIG. 9) in which the first step amplifies the target sequence and the second step adds required 5'UTR and 3'UTR for efficient ITT. Pho4 N or C-His tagged and Cbf1 N or C-His tagged versions were amplified 1 from yeast genomic DNA as follows: The first step PCR reaction contained 1 µM of each gene specific primer, 10 ng µL−1 yeast genomic DNA (SeeGene), 200 µM of each dNTP and 2.5 units of TAQ enzyme mixture (Expand High Fidelity PCR system, Roche) in a final volume of 50 µL. The reaction was cycled for 4 min at 94° C., followed by 30 cycles of 30 s at 94° C., 60 s at 53° C. and 90 s at 72° C. followed by a final extension of 7 min at 72° C. The products were then purified on spin columns (QIAquickPCR, Qiagen) and eluted in 75 µL of 10 mM TrisCl, pH 8.5. The purified product then served as template in the second PCR reaction using 2 µL first PCR product, 5 nM 5'ext1 primer, 5 nM 3'ext2 primer, 200 µM of each dNTP and 2.5 units of TAQ enzyme mixture (Expand High Fidelity PCR system, Roche) in a final volume of 100 µL. The reaction was cycled for 4 min at 94° C. followed by 10 cycles of 30 s at 94° C., 60 s at 53° C. and 90 s at 72° C. followed by a final extension of 72° C. for 7 min. After this first round of extension 2 µL of 5 µM 5'finalCy5 and 5 µM 3'final in dH2O were added to each reaction and cycling was continued immediately at 94° C. for 4 min followed by 30 cycles of 30 sec at 94° C., 60 sec at 50° C. and 90 s at 72° C. followed by a final extension of 72° C. for 7 min. The final product was then purified on spin columns and eluted in 100 µL 10 mM TrisCl, pH8.5 or used directly in ITT reactions. Linear expression templates for MAX iso A, MAX iso B were synthesized essentially as above except that bacterial cDNA clones (MGC) lysed in 2.5 µL Lyse n' Go buffer (Pierce) at 95° C. for 7 min where used as template in an Expand High Fidelity PCR reaction (Roche). The first PCR product was purified using the Qiaquick 96 PCR purification kit (Qiagen) and eluted in 80 µL of 10 mM TrisCl, pH 8.5. To assess the fidelity of these multi-step PCR reactions and to ascertain that no point mutations accumulated during the reaction we submitted final products of MAX iso B notag, MAX iso B C-His, PHO4 C-His and CBF1 N-His to sequencing (Biotech Core). The resulting sequences showed extremely high-fidelity with no accumulation of point mutations (data not shown).

d) Derivatization

During surface derivatization, a circular area is masked with the button while the rest of the surface is passivated with biotinylated bovine serum albumin. When the button is released, the previously protected circular area is specifically derivatized with biotinylated anti-His5 antibody (FIG. 8C-G). After surface patterning the device is loaded with wheat germ based ITT mixture containing linear DNA 5 template coding for the TF to be synthesized and each unit cell is isolated by closing a set of micromechanical valves. The device is incubated at 30° C. for 90 min to complete TF synthesis, solvation of target DNA, and equilibration of TF and target DNA (FIG. 8H-I).

Figure 8G:
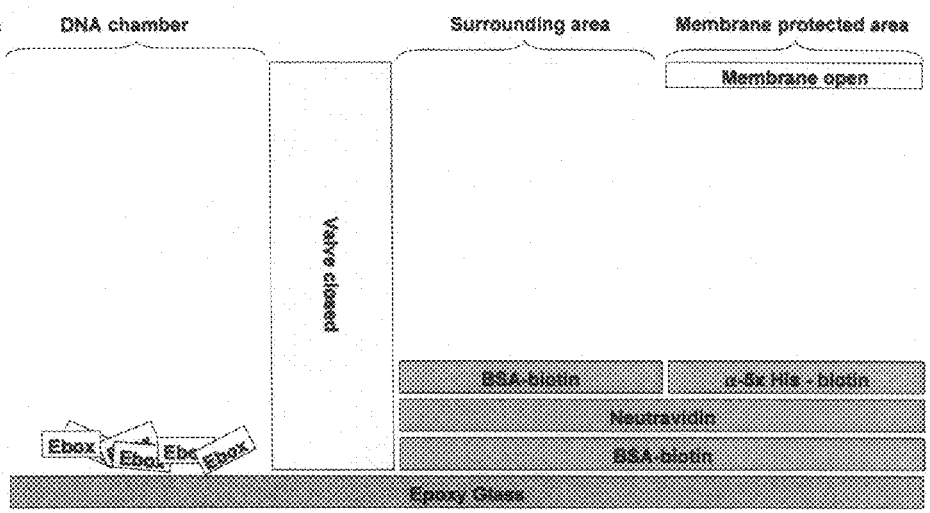
FIG. 8G: Any unbound biotinylated BSA is purged before the "button" membrane is opened again allowing access to the neutravidin surface below to which a biotinylated penta-histidine antibody is attached, concluding the surface derivatization.
Figure 8H:
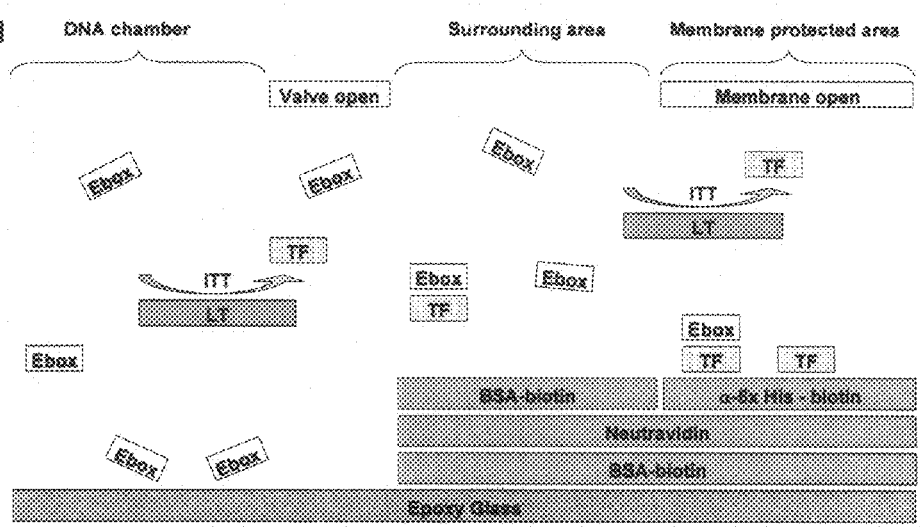
FIG. 8H: ITT programmed with linear expression template is introduced into the device and allowed to flood the DNA chamber causing the solvation of the stored target DNA. Transcription factor is being synthesized and is pulled down to the surface by penta-histidine antibody.
Figure 8I:
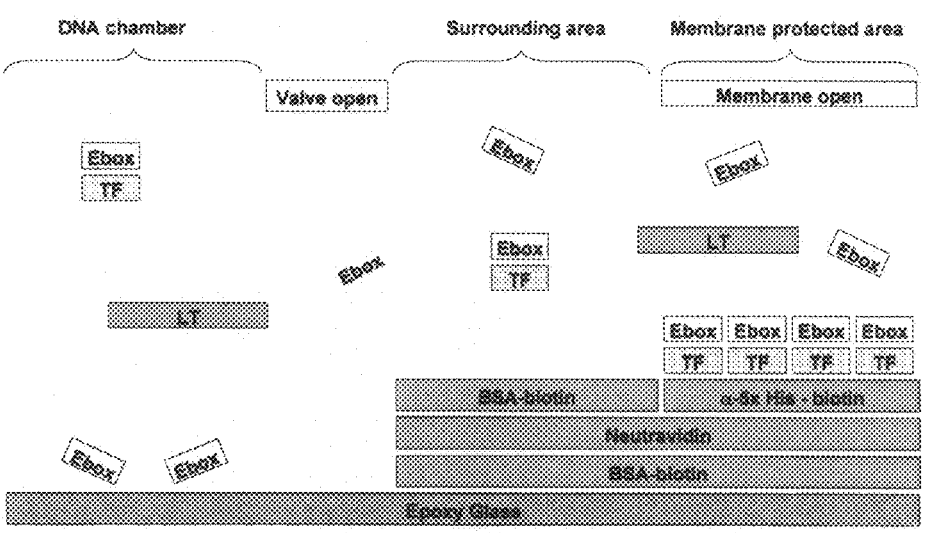
FIG. 8I: The synthesized transcription factors functionally interact with the solvated target DNA pulling it down to the surface as well.

For the initial surface derivatization steps the chamber valves remained closed to prevent liquid from entering the chambers containing the spotted DNA targets (FIG. 8C). First, all accessible surface area was derivatized by flowing a solution of biotinylated BSA (Pierce) resuspended to 2 mg/mL in dH2O for 30 min through all channels, followed by a 10 min PBS wash (FIG. 8D). Next a 500 µg/mL Neutravidin (Pierce) solution in PBS was flown for 20 min, followed by a 10 min PBS wash (FIG. 8E). Next, the "button" membrane was closed and the PBS wash continued for an additional 5 min. Then all remaining accessible surface area was passivated with the same biotinylated solution as above for 30 min, followed by a 10 min PBS wash (FIG. 8F). Finally a 1:1 solution of biotinylated-penta-histidine antibody (Qiagen) in 2% BSA in PBS was loaded for 2-5 min, after which the "button" membrane was opened and flow continued for 20 min, again followed by a 10 min PBS completing the surface derivatization procedure (FIG. 8G).

e) In Vitro Transcription/Translation (ITT)

Following derivatization a standard 25 µL TNT T7 coupled wheat germ extract mixture (Promega) was prepared and spiked with 1 µL tRNALys-bodipy-fl (Promega) and 2 µL of linear expression ready template coding for the appropriate transcription factor. The mixture was immediately loaded onto the device and flushed for 5 min, after which the chamber valves were opened allowing for dead end filling of the chambers with wheat germ extract (FIG. 8H). The chamber valves were again closed and flushing continued for an additional 5 min. Next the segregation valves separating each unit cell were closed followed by opening of the chamber valves allowing for equilibration of the unit cell by diffusion. The entire device was heated to 30° C. on a temperature controlled microscope stage and incubated for up to 90 min (FIG. 8I). After the incubation period the device was imaged on a modified arrayWoRxe (AppliedPrecision) microarray scanner.

f) MITOMI

Figure 8J:
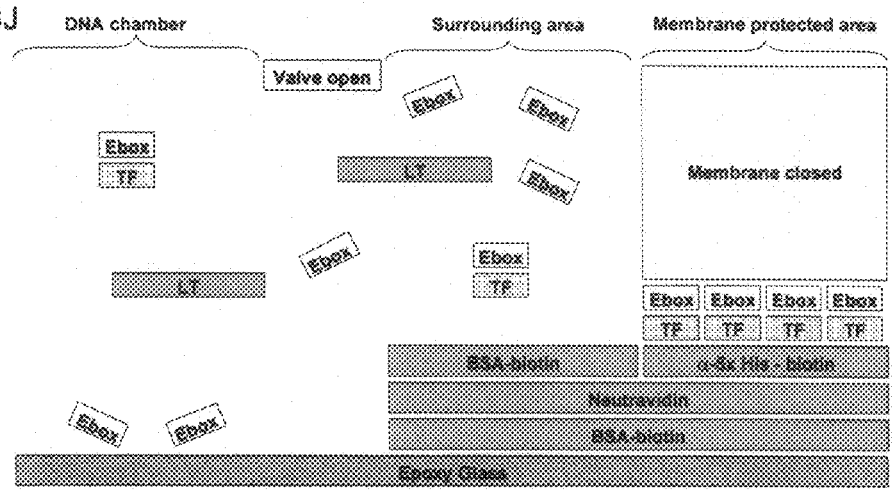
FIG. 8J: After 60-90 min the "button" membrane is closed again mechanically trapping any molecular interactions taking place on the surface allowing all solution phase molecules to be washed away without loss of surface bound material FIGS. 8K-8L.
Figure 8K:
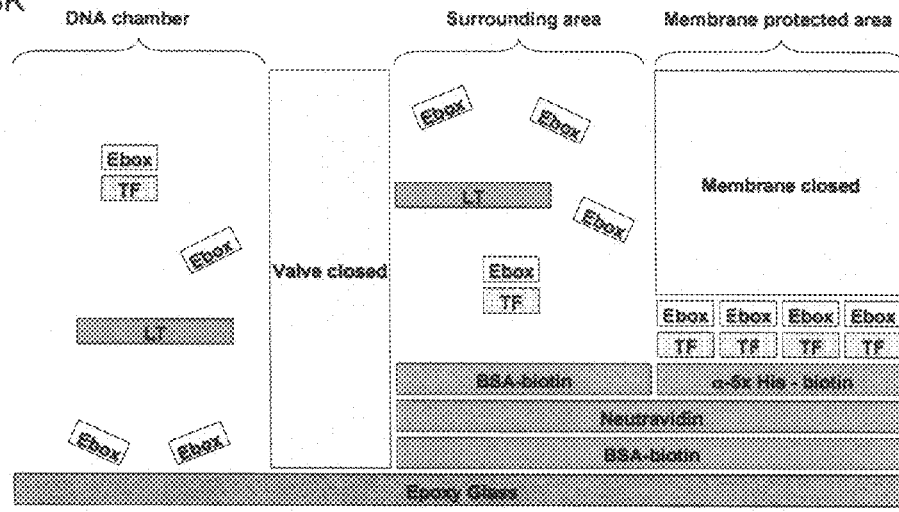
FIG. 8A shows an overview of the experimental approach starting with a plain epoxy substrate to be spotted with 2400 spots of a target DNA library. The finished microarray is then aligned and bonded to one of our microfluidic devices after which the surface is prepared, protein synthesized and MITOMI performed.
FIG. 8B is a micrograph of one of the microfluidic unit cells, shown here again for reference. The dashed lines show which regions of the unit cell are schematically depicted in FIGS. 8C-8L.
FIG. 8C: Before any fluid is introduced into the device the chamber valve (denoted "cv" and colored green in FIG. 8B) is closed to prevent flooding of the DNA chamber.
FIG. 8D: Next biotinylated BSA is introduced into our device which covalently bonds to the epoxy functional groups, both activating (via the biotin moieties) and passivating (epoxy groups) the surface.
FIG. 8E: A solution of neutravidin is introduced forming a monolayer on top of the biotinylated BSA layer.
FIG. 8F: The "button" membrane is closed to protect the detection area from passivation via biotinylated BSA which passivates all accessible surface area.
Figure 8L:
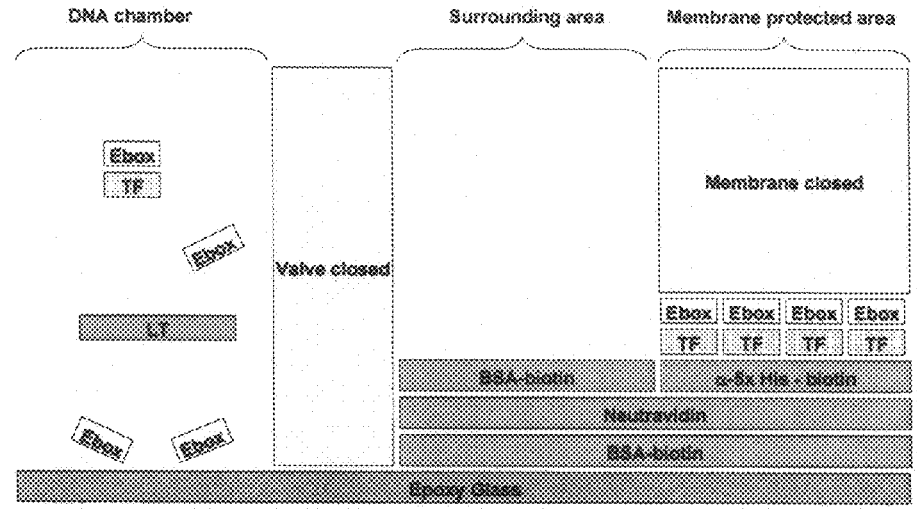

Next we performed MITOMI by closing the "button" membrane (FIG. 8J) as well as the chamber valves (FIG. 8K) followed by a 5 min PBS wash (FIG. 8L) after which the device was imaged once more to detect the trapped molecules. MITOMI characterization To measure the effect of button closing rate on DNA trapping we measured the button closing rates of 640 chamber and 2400 chamber devices. The buttons were closed at various pressures ranging from 12 psi to 24 psi in 3 psi steps to modulate button closing velocities. Movies were taken of the button closing at these various pressures using a digital camera (DFW-V500, Sony) at 25 fps. The radial button closing velocities were extracted from these videos for both devices at all pressures. Closing velocities differ between the two devices due to slight differences in architecture of the button, where the 640 chamber device had a narrower channel connecting the button with the feeding channel. In order to measure the effect of closing velocity on DNA trapping efficiency we measured the resulting ratio of trapped DNA to protein under the button after closing at various velocities. We performed all measurements at closing pressures of 15 psi-18 psi reaching velocities of 4.6 µm/sec and above and thus are in a region were the closing velocity is sufficiently fast and no DNA loss is observed. In order to assess the effectiveness of the mechanical trapping of DNA by the PDMS membrane we measured how much DNA is lost while the button is in a closed state. All experiments were performed on a 640 chamber version of the original device with a TNNNGTG library and MAX iso A C-His as the transcription factor. Two experiments were performed with various measurement intervals. The first experiment consisted of measurement intervals of 30 min for two hours followed by a final long term measurement 15 hours into the experiment. On a second device the measurement interval was extended to 60 min for four hours followed by a final 5 measurement at 21 hours. We then fit exponential functions to all four time-series and plotted the resulting rate constants (not shown). In order to separate the contribution of bleaching to the actual mass loss rate we plotted the measured rate constants as a function of the measurement interval and fit a linear regression, of which the intercept represents the actual mass loss rate with a value of 0.0009 sec$^{-1}$ (not shown). We therefore observe a small mass loss of DNA from beneath the button on very long time scales, most likely due to lateral diffusion, but the loss is negligible over the time course of a normal experiment.

To ascertain the reproducibility of MITOMI we compared experiments from different days and devices for all four TFs studied (not shown). All comparisons show good correlation of values including the low affinity regime. The fact that low affinity measurements correlate indicates that they do not lie near the detection limit, determined to be around 18 μM (data not shown). To arrive at a global measurement error that includes both biological as well as technical noise we compared all N and C-terminally tagged TF datasets, yielding a global measurement error of 19% (not shown). Additional negative controls such as a no protein as well as a no-epitope tag MAX A control showed no non-specific trapping of DNA (data not shown).

Image and Data Analysis

All images were analyzed with GenePix3.0 (Molecular Devices). For each experiment two images where analyzed. The first image taken after the 60-90 min incubation period, was used to determine the concentration of solution phase or total target DNA concentration (Cy5 channel). The second image taken after MITOMI and the final PBS wash was used to determine the concentration of surface bound protein (FITC channel) as well as surface bound target DNA (Cy5 channel). Dissociation equilibrium constants were determined for each experiment using Prism 4 (Graphpad Software) by performing global nonlinear regression fits using a one 6 site binding model to the data plotted as surface bound target DNA (RFU) divided by surface protein concentration (RFU) (or effectively fractional occupancy) as a function of total target DNA concentration (RFU). The Bmax parameter was set equal to the plateau of the consensus sequence and used for all linefits. These relative Kds (RFU-1) were then transformed into absolute Kds (M-1) using a calibration curve previously established by measuring known quantities of 5'CompCy5 primer (data not shown). ΔΔGs were calculated with $\Delta\Delta G=RT^*\ln(Kd/Kd_{ref})$ at a temperature of 298 K. The highest affinity sequence was always chosen as the reference. We estimated our measurement error by plotting affinities measured of all N-terminally tagged transcription factors versus their respective C-terminal variants. We adjusted all slopes of the linear regression fits to be uniform for all transcription factors. Our observed variance was heteroscedastic. We therefore applied a ln transform to our data which resulted in constant variance from which we obtained σ values of 0.17 and 0.40 for one and two σ respectively. Re-transforming these values yields ^σ=0.19x and 2^=0.49× or 19% and 49% respectively.

In Silico Model

Our measurements agree with previous reports that the optimal binding sequence for all four TFs is CACGTG for N-3-N3. We measured consensus binding affinities of 67.0 nM, 73.1 nM, 11.1 nM and 16.6 nM for MAX isoform A, isoform B, Pho4p and Cbf1p, respectively. The binding affinity of MAX to a slightly different sequence has been measured independently and is in agreement with our results for that sequence (Park et al., 2004, *Biochim. Biophys. Acta* 1670: 217). Each binding energy landscape exhibits topographic fine structures such as affinity spikes for sequences with a one base spacer between the two half-sites (CACGGTG for example) as well as consensus neighbors CATGTG, CTCGTG and CAGGTG. These fine structures often lie in the low affinity regime (with off-rates on the order of 2-20 s$^{-1}$) and have thus far not been observed with other methods. The binding energy landscapes for both MAX isoforms are more rugged than the landscapes of Pho4p and Cbf1p, showing strong affinities for consensus neighbors, whereas Pho4p and Cbf1p are singularly specific for the E-box consensus. These differences in topography are intriguing since crystal structures of truncated versions of MAX and Pho4p show 6 that both TFs make essentially the same base specific contacts. Therefore similar base specific contacts give rise to recognition of the same consensus sequence but not necessarily to similar overall binding topographies.

General Materials and Fabrication Methods

The methods used in fabrication of a microfluidic device will vary with the materials used, and include soft lithography methods, microassembly, bulk micromachining methods, surface micro-machining methods, standard lithographic methods, wet etching, reactive ion etching, plasma etching, stereolithography and laser chemical three-dimensional writing methods, modular assembly methods, replica molding methods, injection molding methods, hot molding methods, laser ablation methods, combinations of methods, and other methods known in the art or developed in the future. A variety of exemplary fabrication methods are described in Fiorini and Chiu, 2005, "Disposable microfluidic devices: fabrication, function, and application" Biotechniques 38:429-46; Beebe et al., 2000, "Microfluidic tectonics: a comprehensive construction platform for microfluidic systems." Proc. Natl. Acad. Sci. USA 97:13488-13493; Rossier et al., 2002, "Plasma etched polymer microelectrochemical systems" Lab Chip 2:145-150; Becker et al., 2002, "Polymer microfluidic devices" Talanta 56:267-287; Becker et al., 2000, "Polymer microfabrication methods for microfluidic analytical applications" Electrophoresis 21:12-26; U.S. Pat. No. 6,767,706 B2, e.g., Section 6.8 "Microfabrication of a Silicon Device"; Terry et al., 1979, A Gas Chromatography Air Analyzer Fabricated on a Silicon Wafer, IEEE Trans, on Electron Devices, v. ED-26, pp. 1880-1886; Berg et al., 1994, Micro Total Analysis Systems, New York, Kluwer; Webster et al., 1996, Monolithic Capillary Gel Electrophoresis Stage with On-Chip Detector in International Conference On Micro Electromechanical Systems, MEMS 96, pp. 491-496; and Mastrangelo et al., 1989, Vacuum-Sealed Silicon Micromachined Incandescent Light Source, in Intl. Electron Devices Meeting, IDEM 89, pp. 503-506.

In preferred embodiments, the device is fabricated using elastomeric materials. Fabrication methods using elastomeric materials will only be briefly described here, because elastomeric materials, methods of fabrication of devices made using such materials, and methods for design of devices and their components have been described in detail (see, e.g., Thorsen et al., 2001, "Dynamic pattern formation in a vesicle-generating microfluidic device" *Phys Rev Lett* 86:4163-6; Unger et al., 2000, "Monolithic microfabricated valves and pumps by multilayer soft lithography" Science 288:113-16; Linger et al., 2000, Science 288:113-16; U.S. Pat. No. 6,960, 437 (Nucleic acid amplification utilizing microfluidic devices); U.S. Pat. Nos. 6,899,137 (Microfabricated elastomeric valve and pump systems); 6,767,706 (Integrated active flux microfluidic devices and methods); 6,752,922 (Microfluidic chromatography); 6,408,878 (Microfabricated elastomeric valve and pump systems); 6,645,432 (Microfluidic systems including three-dimensionally arrayed channel networks); U.S. Patent Application publication Nos. 2004/0115838, 20050072946; 20050000900; 20020127736; 20020109114; 20040115838; 20030138829; 20020164816; 20020127736; and 20020109114; PCT patent publications WO 2005/084191; WO05030822A2; and WO 01/01025; Quake & Scherer, 2000, "From micro to nanofabrication with soft materials" Science 290: 1536-40; Xia et al., 1998, "Soft lithography" Angewandte Chemie-International Edition 37:551-575; Unger et al., 2000, "Monolithic microfabricated valves and pumps by multilayer soft lithography" Science 288:113-116; Thorsen et al., 2002, "Microfluidic large-scale integration" Science 298:580-584; Chou et al., 2000, "Microfabricated Rotary Pump" Biomedical Microdevices 3:323-330; Liu et al., 2003, "Solving the "world-to-chip" interface problem with a microfluidic matrix" Analytical Chemistry 75, 4718-23," Hong et al, 2004, "A nanoliter-scale nucleic acid processor with parallel architecture" Nature Biotechnology 22:435-39; Fiorini and Chiu, 2005, "Disposable microfluidic devices: fabrication, function, and application" Biotechniques 38:429-46; Beebe et al., 2000, "Microfluidic tectonics: a comprehensive construction platform for microfluidic systems." Proc. Natl. Acad. Sd. USA 97:13488-13493; Rolland et al., 2004, "Solvent-resistant photocurable "liquid Teflon" for microfluidic device fabrication" J. Amer. Chem. Soc. 126:2322-2323; Rossier et al., 2002, "Plasma etched polymer microelectrochemical systems" Lab Chip 2:145-150; Becker et al., 2002, "Polymer microfluidic devices" Talanta 56:267-287; Becker et al., 2000, "Polymer microfabrication methods for microfluidic analytical applications" Electrophoresis 21:12-26; Terry et al., 1979, A Gas Chromatography Air Analyzer Fabricated on a Silicon Wafer, IEEE Trans, on Electron Devices, v. ED-26, pp. 1880-1886; Berg et al., 1994, Micro Total Analysis Systems, New York, Kluwer; Webster et al., 1996, Monolithic Capillary Gel Electrophoresis Stage with On-Chip Detector in International Conference On Micro Electromechanical Systems, MEMS 96, pp. 491-496; and Mastrangelo et al., 1989, Vacuum-Sealed Silicon Micromachined Incandescent Light Source, in Intl. Electron Devices Meeting, IDEM 89, pp. 503-506; and other references cited herein and found in the scientific and patent literature.

Methods of fabrication of complex microfluidic circuits using elastomeric are known and are described in Unger et al., 2000, Science 288:113-116; Quake & Scherer, 2000, "From micro to nanofabrication with soft materials" Science 290: 1536-40; Xia et al., 1998, "Soft lithography" Angewandte Chemie-international Edition 37:551-575; Unger et al., 2000, "Monolithic microfabricated valves and pumps by multilayer soft lithography" Science 288:113-116; Thorsen et al., 2002, "Microfluidic large-scale integration" Science 298:580-584; Chou et al., 2000, "Microfabricated Rotary Pump" Biomedical Microdevices 3:323-330; Liu et al., 2003, "Solving the "world-to-chip" interface problem with a microfluidic matrix" Analytical Chemistry 75, 4718-23," and other references cited herein and known in the art.

Although the present invention has been described in detail with reference to specific embodiments, those of skill in the art will recognize that modifications and improvements are within the scope and spirit of the invention, as set forth in the claims which follow. All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

SEQUENCE LISTING

```
<160> NUMBER OF SEQ ID NOS: 2

<210> SEQ ID NO 1
<211> LENGTH: 85
<212> TYPE: DNA
<213> ORGANISM: Artificial
<220> FEATURE:
<223> OTHER INFORMATION: 5' UTR region added by two step PCR method

<400> SEQUENCE: 1
gatcttaagg ctagagtact aatacgactc actataggga atacaagcta cttgttcttt      60
ttgcactcga gaattcgcca ccatg                                           85

<210> SEQ ID NO 2
<211> LENGTH: 100
<212> TYPE: DNA
<213> ORGANISM: Artificial
<220> FEATURE:
<223> OTHER INFORMATION: 3' UTR region added by two step PCR method

<400> SEQUENCE: 2
```

-continued

```
taataacgac tcaggctgct acaaaaaaaa aaaaaaaaaa aaaaaaaaaa aactagcata        60 acccottggg gcctctaaac gggtcttgag gggtttttg                              100
```

The invention claimed is:

1. A method for selectively modifying a substrate in a chamber or channel of a unit cell of a microfluidic device comprising
   (i) masking a first portion of the substrate by contacting the first portion with a moveable element of the unit cell and leaving other portions of the substrate non-masked;
   (ii) contacting non-masked portions of the substrate with a substrate modifying agent that modifies the non-masked portions of the substrate leaving the first portion unmodified;
   (iii) depleting or removing the substrate modifying agent; and then
   (iv) unmasking the first portion of the substrate.

2. The method of claim 1 wherein the movable element is a deflectable elastomeric membrane.

3. The method of claim 2 wherein the membrane is free-standing.

4. The method of claim 3 wherein contact between the membrane and the substrate occurs medially and extends radially outward such that the non-masked portion surrounds the masked portion.

5. The method of claim 1 wherein the substrate modifying agent covalently modifies the substrate.

6. The method of claim 1 wherein the substrate modifying agent noncovalently modifies the substrate.

7. The method of claim 6 wherein the substrate modifying agent is a protein or a nucleic acid.

8. The method of claim 7 wherein the substrate modifying agent is an antibody, a receptor, a fusion protein, a glycan, a lipid, or a carbohydrate.

9. The method of claim 8 wherein the substrate modifying agent is conjugated to avidin or biotin.

10. The method of claim 1 wherein the substrate has previously been selectively modified.

* * * * *